United States Patent
Boyd et al.

(10) Patent No.: US 12,076,424 B2
(45) Date of Patent: *Sep. 3, 2024

(54) GLASS COMPOSITION

(71) Applicant: IR Scientific Inc., Halifax (CA)

(72) Inventors: Daniel Boyd, Upper Tantallon (CA); Kathleen O'Connell, Halifax (CA); Kathleen Naomi MacDonald-Parsons, Bedford (CA)

(73) Assignee: IR SCIENTIFIC INC., Halifax (CA)

(*) Notice: Subject to any disclaimer, the term of this patent is extended or adjusted under 35 U.S.C. 154(b) by 0 days.

This patent is subject to a terminal disclaimer.

(21) Appl. No.: 17/273,661

(22) PCT Filed: Sep. 4, 2019

(86) PCT No.: PCT/CA2019/051237
§ 371 (c)(1),
(2) Date: Mar. 4, 2021

(87) PCT Pub. No.: WO2020/047662
PCT Pub. Date: Mar. 12, 2020

(65) Prior Publication Data
US 2021/0259933 A1    Aug. 26, 2021

Related U.S. Application Data

(60) Provisional application No. 62/847,807, filed on May 14, 2019, provisional application No. 62/727,377, filed on Sep. 5, 2018.

(51) Int. Cl.
*A61K 8/21* (2006.01)
*A61K 6/30* (2020.01)
(Continued)

(52) U.S. Cl.
CPC .......... *A61K 8/21* (2013.01); *A61K 6/30* (2020.01); *A61K 8/042* (2013.01); *A61K 8/27* (2013.01);
(Continued)

(58) Field of Classification Search
CPC . A61K 8/21; A61K 6/30; A61K 8/042; A61K 8/27; A61K 8/0241; A61K 8/19;
(Continued)

(56) References Cited

U.S. PATENT DOCUMENTS

| 3,829,331 A | 8/1974 | Tsang |
| 3,834,912 A | 9/1974 | Gliemeroth |

(Continued)

FOREIGN PATENT DOCUMENTS

| CA | 2361573 A1 | 8/2000 |
| CA | 2965308 A1 | 4/2016 |

(Continued)

OTHER PUBLICATIONS

Machine translation of JP2000-264677A, 2000, machine translation retrieved Jun. 2, 2022 from https://www.j-platpat.inpit.go.jp (Year: 2000).*

(Continued)

*Primary Examiner* — Adam C Milligan
*Assistant Examiner* — Amanda Michelle Petritsch
(74) *Attorney, Agent, or Firm* — Borden Ladner Gervais LLP; David Nauman

(57) ABSTRACT

The present disclosure provides a glass composition that include from about 50 mol % to about 95 mol % of B2O3; from about 5 mol % to about 50 mol % of one or more glass components selected from the group consisting of: Li2O, Rb2O, K2O, Na2O, SrO, CaO, MgO, and ZnO. The glass composition includes less than 30 mol % of Rb2O. The glass composition is a quaternary system. The glass composition (Continued)

is a particulate material that includes particles that are from about 1 to about 50 μm in size. The glass composition loses at least 5 mass % within 24 hours when exposed to a buffered saline solution. The glass composition may be used to desensitize dentin. The present disclosure also provides a dentin-desensitizing composition.

8 Claims, 12 Drawing Sheets

(51) Int. Cl.
  *A61K 8/04*  (2006.01)
  *A61K 8/27*  (2006.01)
  *A61Q 11/00*  (2006.01)
  *C03C 3/14*  (2006.01)
  *C03C 3/23*  (2006.01)
  *C03C 4/00*  (2006.01)
  *C03C 12/00*  (2006.01)

(52) U.S. Cl.
  CPC .............. *A61Q 11/00* (2013.01); *C03C 3/14* (2013.01); *C03C 3/23* (2013.01); *C03C 4/0021* (2013.01); *C03C 12/00* (2013.01); *C03C 2204/00* (2013.01)

(58) Field of Classification Search
  CPC ...... A61K 8/25; A61K 6/20; A61K 2800/412; A61K 33/00; A61K 33/16; A61K 33/08; A61K 33/22; A61K 33/30; A61P 1/02; A61Q 11/00; C03C 3/14; C03C 3/23; C03C 4/0021; C03C 12/00; C03C 2204/00; C03C 3/247
  See application file for complete search history.

(56) References Cited

U.S. PATENT DOCUMENTS

| | | | |
|---|---|---|---|
| 4,174,334 A * | 11/1979 | Bertenshaw | A61L 27/446 106/35 |
| 4,250,277 A | 2/1981 | Maries et al. | |
| 4,340,693 A | 7/1982 | Drake et al. | |
| 4,507,369 A | 3/1985 | Badzioch | |
| 5,112,777 A | 5/1992 | MacDowell | |
| 5,153,070 A | 10/1992 | Andrus et al. | |
| 5,735,942 A | 4/1998 | Litkowski et al. | |
| 6,187,701 B1 | 2/2001 | Sekino et al. | |
| 6,214,471 B1 | 4/2001 | Beall et al. | |
| 6,360,562 B1 | 3/2002 | Kodas et al. | |
| 6,709,744 B1 | 3/2004 | Day et al. | |
| 6,993,934 B2 | 2/2006 | Kodas et al. | |
| 7,208,430 B2 | 4/2007 | Hasegawa et al. | |
| 7,631,518 B2 | 12/2009 | Kodas et al. | |
| 7,709,027 B2 | 5/2010 | Fechner et al. | |
| 7,749,929 B2 | 7/2010 | Tanida et al. | |
| 7,799,714 B2 | 9/2010 | Fujiwara | |
| 8,287,896 B2 | 10/2012 | Jung et al. | |
| 8,481,066 B2 | 7/2013 | Day et al. | |
| 8,715,625 B1 * | 5/2014 | Rokitowski | A61K 8/9739 501/63 |
| 8,821,919 B2 | 9/2014 | Jung | |
| 9,173,822 B2 | 11/2015 | Fechner et al. | |
| 9,238,044 B2 | 1/2016 | Da Fonte Ferreira et al. | |
| 9,486,554 B2 | 11/2016 | Jung et al. | |
| 10,507,263 B2 | 12/2019 | Nazhat et al. | |
| 10,624,994 B2 | 4/2020 | Bakry | |
| 2003/0228471 A1 | 12/2003 | Hayakawa et al. | |
| 2004/0234462 A1 | 11/2004 | Algar et al. | |
| 2009/0075083 A1 | 3/2009 | Bi et al. | |
| 2011/0165221 A1 | 7/2011 | Jung et al. | |
| 2014/0271912 A1 | 9/2014 | Pomrink et al. | |
| 2017/0196666 A1 | 7/2017 | Böhm et al. | |
| 2017/0342382 A1 | 11/2017 | Deng et al. | |
| 2017/0349876 A1 | 12/2017 | Deng et al. | |
| 2019/0161392 A1 | 5/2019 | Deng et al. | |
| 2019/0161393 A1 | 5/2019 | Deng et al. | |

FOREIGN PATENT DOCUMENTS

| | | | | |
|---|---|---|---|---|
| CA | 3135513 A1 | 10/2020 | | |
| CN | 101094818 A | 12/2007 | | |
| CN | 102247599 A | 11/2011 | | |
| CN | 102781410 A | 11/2012 | | |
| CN | 103936281 A | 7/2014 | | |
| CN | 107250074 A | 10/2017 | | |
| CN | 108164135 A | 6/2018 | | |
| JP | S5884144 A | 5/1983 | | |
| JP | H07257938 A | 10/1995 | | |
| JP | 2000095544 A | 4/2000 | | |
| JP | 2000264677 A * | 9/2000 | ........... | C03C 14/004 |
| JP | 2003146697 A | 5/2003 | | |
| JP | 2009084137 A | 4/2009 | | |
| JP | 2011168516 A | 9/2011 | | |
| JP | 5782429 B2 | 9/2015 | | |
| JP | 2015227311 A | 12/2015 | | |
| WO | 0044681 A2 | 8/2000 | | |
| WO | 2004076369 A2 | 9/2004 | | |
| WO | 2005060921 A1 | 7/2005 | | |
| WO | 2007144662 A1 | 12/2007 | | |
| WO | 2010115039 A2 | 10/2010 | | |
| WO | WO-2011085092 A1 * | 7/2011 | ....... | A61F 13/00008 |
| WO | 2011161422 A1 | 12/2011 | | |
| WO | 2014154874 A3 | 10/2014 | | |
| WO | 2017205570 A1 | 11/2017 | | |
| WO | 2020047662 A1 | 3/2020 | | |

OTHER PUBLICATIONS

Sokolov, et al., "Influence of MeF2 (Me = Mg, Ca, Sr, and Ba) on the Electrical Properties of Glasses in the MeF2—Na2B4O7 System," Glass Physics and Chemistry, Jul. 2000, vol. 26 (4), pp. 383-389. (Year: 2000).*

Pizzorno, L., "Nothing Boring About Boron," Integrative Medicine, Aug. 2015, vol. 14 (4), pp. 35-48.

Wright, A., "My Borate Life: An Enigmatic Journey", International Journal of Applied Glass Science, vol. 6(1), Mar. 2015, pp. 45-63.

Food and Drug Administration, "Proposed Rule: Oral Health Care Drug Products for Over-the-Counter Human Use; Amendment to Tentative Final Monograph to Include OTC Relief of Oral Discomfort Drug Products", Federal Register, vol. 56 (185), Sep. 2001, pp. 48301-48347.

Rainey et al., "Daily Boron Intake From the American Diet," Journal of the American Dietetic Association, Mar. 1999, vol. 99 (3), pp. 335-340.

Reeder et al., "Dentin Permeability: Determinants of Hydraulic Conductance," Journal of Dental Research, Feb. 1978, vol. 57 (2), pp. 187-193.

Ren, et al., "Sintering Behavior and Microwave Dielectric Properties of B2O3—La2O3—MgO—TiO2 Based Glass-ceramic for LTCC Applications," Materials Letters, Jan. 2018, vol. 210, pp. 113-116.

Salehi et al., "Cytotoxicity of Resin Composites Containing Bioactive Glass Fillers," Dental Materials, Feb. 2015, vol. 31 (2), pp. 195-203.

Sandle, T., "A Comparative Study of Different Methods for Endotoxin Destruction," American Pharmaceutical Review, Nov. 2013, vol. 16 (6), pp. 15-17.

Santonen et al., "Review on Toxicity of Stainless Steel", In: Finnish Institute of Occupational Health, Helsinki, Finland, Nov. 2010, 87 pages.

Saranti, et al. "Bioactive Glasses in the System CaO—B2O3—P2O5: Preparation, Structural Study and in Vitro Evaluation", Journal of Non-Crystalline Solids, May 2006, vol. 352(5), pp. 390-398.

Sarikaya et al., "Evaluation of Genotoxic and Antigenotoxic Effects of Boron by the Somatic Mutation and Recombination Test (SMART) on *Drosophila*," Drug and Chemical Toxicology, Oct. 2016, vol. 39(4), pp. 400-406.

(56) References Cited

OTHER PUBLICATIONS

Sayyadi-Shahraki, et al., "Microwave Dielectric Properties and Chemical Compatibility With Silver Electrode of Li2TiO3 Ceramic With Li2O—ZnO—B2O3 Glass Additive," Physica B, Jan. 2015, vol. 457, pp. 57-61.
SCCS (Scientific Committee on Consumer Safety), "Opinion on the Safety of Boron Compounds in Cosmetic Products", European Commission, Luxembourg; Dec. 2013, doi: 10.2772/7521.
Scott, et al., "Ames Positive Boronic Acids Are Not All Eukaryotic Genotoxins," Mutation Research/Genetic Toxicology and Environmental Mutagenesis, Jan. 2015, vol. 777, pp. 68-72.
Sharma, et al., "A Novel Potassium Oxalate-containing Toothdesensitising Mouthrinse: a Comparative in Vitro Study," Journal of Dentistry, Jul. 2013, vol. 44(4), pp. S18-S27.
Amaechi and Van Loveren, "Fluorides and Non-fluoride Remineralization Systems," In: Toothpastes, Monographs in Oral Science, Amsterdam, Netherlands; 2013, vol. 23, pp. 15-26.
Thind, et al. "Structural and Acoustic Investigations of Calcium Borate Glasses", Physica Status Solidi (a), Aug. 2006, vol. 203(10), pp. 2356-2364.
US Food and Drug Administration (USFDA), "Q3D Elemental Impurities Guidance for Industry", In: U.S. Department of Health and Human Services FDA, Center for Drug Evaluation and Research, Center for Biologics Evaluation and Research, editor.; Sep. 2015, 85 pages.
US Environmental Protection Agency, "Integrated Risk Information System (IRIS), Chemical Assessment Summary: Boron and Compounds" (CASRN 7440-42-8), Aug. 2004, 29 pages.
Kamitsos, E.I., "Modifying Role of Alkali-Metal Cations in Borate Glass Networks", The Journal of Physical Chemistry, vol. 93(4), Feb. 1989, pp. 1604-1611.
Kijsamanmith et al., "Comparison of Milk and Desensitizing Dentifrices in Reducing Hydraulic Conductance of Human Dentin in Vitro," Southeast Asian Journal of Tropical Medicine and Public Health, Mar. 2018, vol. 49 (2), pp. 345-354.
Kokubo et al., "How Useful is SBF in Predicting in Vivo Bone Bioactivity?", Biomaterials, May 2006, vol. 27 (15), pp. 2907-2915.
Li et al., "Bioactive Glasses: Traditional and Prospective Applications in Healthcare," In: Hot Topics in Biomaterials, Future Medicine Ltd., Feb. 2014, pp. 56-68, DOI: https://doi.org/10.4155/ebo.13.585.
Li et al., "Silver Co-Firable ZnTiNb2O8 Microwave Dielectric Ceramics With Li2O—ZnO—B2O3 Glass Additive," International Journal of Applied Ceramic Technology, Apr. 2010, vol. 7 (S1), pp. E144-E150.
Lim et al., "Enhanced Elevated-Temperature Performance of Li(Ni0.8co0.015al0.05)o2 Electrodes Coated With 12)-2B2O3 Glass," Electrochimica Acta, Aug. 2014, vol. 136, pp. 1-9.
Litkowski, Leonard, "Prevent Tooth Pain and Sensitivity With the Latest Tooth Protection Technology," CDA Essentials, 2018, vol. 5(2), pp. 28-29.
Litovitz et al., "Clinical Manifestations of Toxicity in a Series of 784 Boric Acid Ingestions," The American Journal of Emergency Medicine, May 1988, vol. 6(3), pp. 209-213.
Lung et al., "Boiled Lobster Rash of Acute Boric Acid Toxicity," Clinical Toxicology, Jun. 2009, vol. 47 (5), p. 432.
Macon et al., "A Unified in Vitro Evaluation for Apatite-forming Ability of Bioactive Glasses and Their Variants," Journal of Materials Science: Materials in Medicine, Feb. 2015, vol. 26 (2), pp. 115-124.
Manam et al., "Study of Corrosion in Biocompatible Metals for Implants: A Review," Journal of Alloys and Compounds, Apr. 2017, vol. 701, pp. 698-715.
Mantzourani et al., "Detine Sensitivity: Past, Present and Future," Journal of Dentistry, Jul. 2013, vol. 41 (4), pp. s3-s17.
Manupriya et al., "Compositional Dependence of in-Vitro Bioactivity in Sodium Calcium Borate Glasses," Journal of Physics and Chemistry of Solids, Aug. 2009, vol. 70, pp. 1137-1141.

Narwal et al. "Dy3+ doped LiCi—CaO—BiO3—B2O3 Glasses for WLED applications", Ceramics International, vol. 43 (13), Oct. 2017, pp. 11132-11141.
O'Connell et al., "High Borate Networks as a Platform to Modulate Temporal Release of Therapeutic Metal Ions Gallium and Strontium," Biomedical Glasses, Apr. 2017, vol. 3 (1), pp. 18-29.
O'Connell et al., "Linear Release of Strontium Ions From High Borate Glasses via Lanthanide/alkali Substitutions," Journal of Non-Crystalline Solids, Dec. 2015, vol. 430, pp. 1-8.
Pajor et al., "Hydroxyapatite and Fluorapatite in Conservative Dentistry and Oral Implantology—A Review," Materials, Aug. 2019, vol. 12(17), pp. 1-16.
Patel et al., "Comparison of the Effects on Dentin Permeability of Two Commercially Available Sensitivity Relief Dentifrices," The Journal of Clinical Dentistry, Oct. 2011, vol. 22(4), pp. 108-112.
Faroon, et al., "Toxicological Profile for Acetone", Agency for Toxic Substances and Disease Registry (ATSDR) Toxicological Profiles, U.S. Department of Health and Human Services, May 1994, pp. 1-206, Atlanta, Georgia, USA.
American Dental Association Council on Scientific Affairs, "Fluoride Toothpaste Use for Young Children," Journal of the American Dental Association, Feb. 2014, vol. 145 (2), pp. 190-191.
Zhong et al., "Change in Boron Coordination in Alkali Borate Glasses, and Mixed Alkali Effects, as Elucidated by NMR", Journal of Non-Crystalline Solids, Sep. 1989, vol. 111 (1), pp. 67-76.
Bakri et al., "Dentinal Tubules Occluded by Bioactive Glasscontaining Toothpaste Exhibit High Resistance Toward Acidic Soft Drink Challenge," Australian Dental Journal, Jun. 2017, vol. 62 (2), pp. 186-191.
Barbafieri et al., "Contaminant Bioavailability in Soil and Phytotoxicity/genotoxicity Tests in *Vicia faba* L.: a Case Study of Boron Contamination," Environmental Science and Pollution Research International, Sep. 2016, vol. 23(23), pp. 24327-24336.
Biomin Technologies Ltd., "How is BioMin® different from NovaMin®?", web page: <https://www.biomin.co.uk/science-information/bioactive-glasses/biomintm-vs-novaminr>, 2020, 4 pages.
Blevins et al., "Boron in Plant Structure and Function," Annual Review of Plant Physiology and Plant Molecular Biology, Jun. 1998, vol. 49(1), pp. 481-500.
Borm et al., "The carcinogenic action of crystalline silica: a review of the evidence supporting secondary inflammation-driven genotoxicity as a principal mechanism", Critical Reviews in Toxicology, Oct. 2011, vol. 41(9), pp. 756-770.
British Dental Association, "Targeted Pain Relief for Dentine Hypersensitivity", British Dental Journal, vol. 221(8), Oct. 2016, pp. 530.
Camps et al., "Low Versus High Pressure for in Vitro Determination of Hydraulic Conductance of Human Dentine," Archives of Oral Biology, Jan. 1997, vol. 42(4), pp. 293-298.
Charoenlarp et al., "Pain and the Rate of Dentinal Fluid Flow Produce by Hydrostatic Pressure Stimulation of Exposed Dentine in Man," Archives of Oral Biology, Jul. 2007, vol. 52(7), pp. 625-631.
Divina, et al. "Physical, Structural, and Radiation Shielding Properties of B2O3—MgO—K2O—Sm2O3 Glass Network Modified With Teo2", Radiation Physics Chemistry, Jul. 2019, vol. 160, pp. 75-82.
Dourson et al., "Regulatory History and Experimental Support of Uncertainty (Safety) Factors," Regulatory Toxicology and Pharmacology, Sep. 1983, vol. 3 (3), pp. 224-238.
Dourson et al., "Chapter 28: The Use of Uncertainty Factors in Establishing Safe Levels of Exposure", In: Krewski D, Franklin C, editors; Statistics in Toxicology, New York, NY: Gordon and Breach Science Publishers; 1991, pp. 613-627.
European Committee for Standardization, "Dentistry—Dentrifrices—Requirements, test methods, and marking (EN ISO 11609:2017)", Estonian Centre for Standardization, Jun. 2017, 32 pages.
European Union, "Disodium Tetraborate, Anhydrous Boric Acid, Boric Acid, Boric Acid, Crude Natural", European Union Draft Risk Assessment Report, Nov. 2009, 341 pages, retrieved from <https://echa.europa.eu/documents/10162/ea3533df-1457-4664-98d6-51b2f904af36>.
European Patent Application No. 19858112.6, Extended European Search Report dated May 13, 2022.

(56) References Cited

OTHER PUBLICATIONS

Institute of Medicine, "Dietary Reference Intakes for Calcium and Vitamin D", In: Ross, Taylor, Yaktine and Del Valle, editors; Washington, DC: The National Academies Press, 2011, 662 pages.

Geanta et al., "Stainless Steels With Biocompatible Properties for Medical Devices" Key Engineering Materials, vol. 583, Trans Tech Publications, Sep. 2013, pp. 9-15.

Gülsoy et al., "Genotoxic Effects of Boric Acid and Borax in Zebrafish, Danio Rerio Using Alkaline Comet Assay," Excli Journal, Jul. 2015, vol. 14, pp. 890-899.

Greenhill et al., "The Effects of Desensitizing Agents on the Hydraulic Conductance of Human Dentin in Vitro," Journal of Dental Research, Mar. 1981, vol. 60 (3), pp. 686-698.

Hasan et al., "Composition-Structure-Properties Relationship of Strontium Borate Glasses for Medical Applications," Journal of Biomedical Materials Research Part A, Jul. 2015, vol. 103 (7), pp. 1-11.

Hill et al., "An in Vitro Comparison of a Novel Self-Assembling Peptide Matrix Gel and Selected Desensitizing Toothpastes in Reducing Fluid Flow by Dentine Tubular Occlusion," Journal of Dental and Maxillofacial Research, Feb. 2020, vol. 3 (1), pp. 1-11.

Huang et al., "Effect of Nano-hydroxyapatite Concentration on Remineralization of Initial Enamel Lesion in Vitro," Biomedical Materials, Jun. 2009, vol. 4 (3), pp. 1-6.

Humphrey et al., "A Review of Saliva: Normal Composition, Flow, and Function," The Journal of Prosthetic Dentistry, Feb. 2001, vol. 85 (2), pp. 162-169.

Ince et al., "Protective Effects of Boron on Cyclophosphamide Induced Lipid Peroxidation and Genotoxicity in Rats," Chemosphere, Aug. 2014, vol. 108, pp. 197-204.

International Patent Application No. PCT/CA2021/051237 International Search Report and Written Opinion dated Nov. 22, 2019.

Yiannopoulos et al., "Structure and properties of Alkaline Earth Borate Glasses", Physics and Chemistry of Glasses, vol. 42(3), Jun. 2001, pp. 164-172.

Yi et al., "A Carbonate-fluoride Defect Model for Carbonate-rich Fluorapatite," American Mineralogist, Mineralogical Society of America, May 2013, vol. 98(5-6), pp. 1066-1069.

International Standard, "Implants for Surgery—In Vitro Evaluation for Apatite-Forming Ability of Implant Materials", ISO 23317 (Third Edition), Jun. 2014, 14 pages.

Joao-Souza et al., "Effectiveness and Acid/tooth Brushing Resistance of in-office Desensitizing Treatments—A Hydraulic Conductance Study," Archives of Oral Biology, Dec. 2018, vol. 96, pp. 130-136.

João-Souza et al., "Influence of Desensitizing and Anti-Erosive Toothpastes on Dentine Permeability: An in Vitro Study," Journal of Dentistry, Oct. 2019, vol. 89, pp. 1-18.

Indian Patent Application No. 202117010608, Office Action dated Mar. 13, 2023.

Sokolov, et al., "Influence of MeF2 (Me = Mg, Ca, Sr, and Ba) on the Electrical Properties of Glasses in the MeF2—Na2B4O7 System," Glass Physics and Chemistry, Jul. 2000, vol. 26 (4), pp. 383-389.

Wright, "Borate Structures: Crystalline and Vitreous," Physics and Chemistry of Glasses: European Journal of Glass Science and Technology Part B, Feb. 2010, vol. 51(1), pp. 1-39.

Taiwan Patent Application No. TW20190131921, Office Action dated May 2, 2023 and English Translation.

Brazilian Patent Application No. BR 11 2021 004219 9, Office Action dated Jun. 16, 2023 and English Translation.

Canadian Patent Application No. 3,111,638, Office Action dated Feb. 22, 2024.

Chinese Patent Application No. 201980058257.3, Office Action dated Jan. 10, 2024 and English Translation.

Indian Patent Application No. 202117010608, Hearing Notice dated Mar. 22, 2024.

European Patent Applicant No. 19858112.6, Office Action dated Jan. 4, 2024.

Korean Patent Application No. 10-2021-7009852, Office Action dated Jan. 10, 2024 and English Translation.

Pronkin, et al., "Concentration Dependence of Electric Conductivity for Fluorine-Containing Sodium Borate Glasses", Glass Physics and Chemistry, May 2000, vol. 26(3), pp. 268-273.

Shelby et al., "Properties and Structure of NaF—Na2O—B2O3 Glasses," Physics and Chemistry of Glasses, Feb. 1990, vol. 31(1), pp. 25-29.

Japanese Patent Application No. JP2021512902, Office Action dated Sep. 26, 2023 and English Translation.

Taiwanese Patent Application No. TW20190131921, Office Action dated Oct. 13, 2023 and English Translation.

Raju, et al., "Structural and Optical Investigations of Eu3+ Ions in Lead Containing Alkali Fluoroborate Glasses," Optical Materials, Feb. 2012, vol. 34(8), pp. 1251-1260.

Ota, et al., "Crystallization Behavior in Oxyfluoroborate Glass," Japan Ceramics Association Academic Textile Magazine, Apr. 1990, vol. 98, pp. 1125-1131.

Australian Patent Application No. 2019335429, Examination Report dated Jun. 25, 2024.

\* cited by examiner

GLASS COMPOSITION

FIELD

The present disclosure relates to glass compositions for dentin-desensitizing compositions.

BACKGROUND

The following paragraphs are not an admission that anything discussed in them is prior art or part of the knowledge of persons skilled in the art.

Dentin sensitivity is dental pain that arises from exposed dentin surfaces in response to stimuli, such as thermal, evaporative, tactile, osmotic, chemical or electrical. Dentin sensitivity may be caused by gingival recession (receding gums) with exposure of root surfaces, loss of the cementum layer and smear layer, tooth wear, acid erosion, periodontal root planing, or dental bleaching.

Dentine contains many thousands of microscopic tubular structures that radiate outwards from the pulp. Changes in the flow of the plasma-like biological fluid present in the dentinal tubules can trigger mechanoreceptors present on nerves located at the pulpal aspect, thereby eliciting a pain response. This hydrodynamic flow can be increased by cold, air pressure, drying, sugar, sour (dehydrating chemicals), or forces acting onto the tooth. Hot or cold food or drinks, and physical pressure are typical triggers in those individuals with teeth sensitivity.

There is no universally accepted, gold-standard treatment which reliably relieves the pain of dental hypersensitivity in the long term. However, treatments can be divided into in-office (i.e. intended to be applied by a dentist or dental therapist), or treatments which can be carried out at home, available over-the-counter or by prescription.

The purported mechanism of action of these treatments is either occlusion of dentin tubules, or desensitization of nerve fibres/blocking the neural transmission.

INTRODUCTION

The following introduction is intended to introduce the reader to this specification but not to define any invention. One or more inventions may reside in a combination or sub-combination of the apparatus elements or method steps described below or in other parts of this document. The inventors do not waive or disclaim their rights to any invention or inventions disclosed in this specification merely by not describing such other invention or inventions in the claims.

One example of a dentin-desensitizing composition known in the art is disclosed in PCT Publication No. WO2007144662A1. The disclosed toothpaste includes a bioactive glass comprising strontium. The disclosed bioactive glass occludes dentin tubules and induces precipitation and crystallisation of a carbonated hydroxyapatite. The disclosed bioactive glass is designed to degrade at the same rate as the rate of the induced tissue ingrowth.

One example of a dentin-desensitizing composition known in the art is disclosed in U.S. Pat. No. 5,735,942. The disclosed toothpaste includes a mineral composition composed of CaO, $Na_2O$, $P_2O_5$ and $SiO_2$. The disclosed mineral composition chemically reacts with the surface of dentin and intimately bonds to tooth structure.

One or more described embodiments attempt to address or ameliorate one or more shortcomings involved with dentin-desensitizing compositions that include non-degradable particulate material that occludes dentin tubules. In some embodiments, the disclosed particulate material substantially degrades over a period between 12 and 24 hours under environmental conditions. In some embodiments, the disclosed particulate material provides a controlled release of fluoride over the same time period.

In some embodiments, the present disclosure provides a glass composition that includes from about 50 mol % to about 95 mol % of $B_2O_3$; from about 5 mol % to about 50 mol % of a glass component selected from the group consisting of: $Li_2O$, $Rb_2O$, $K_2O$, $Na_2O$, SrO, CaO, MgO, ZnO and any combination thereof; 0 mol % of CuO; less than 0.1 mol % of BaO; and less than 0.1 mol % of $P_2O_5$; where the glass composition comprises less than 30 mol % of $Rb_2O$. The glass composition loses at least 5 mass % within 24 hours when exposed to a buffered saline solution, and the glass composition is a particulate material that comprises particles that are from about 1 to about 50 μm in size. The glass composition does not consist solely of $B_2O_3$ and $Na_2O$.

In some examples of glass compositions according to the present disclosure, less than 20 mol %, such as less than 15 mol %, less than 10 mol %, or less than 5 mol % of the glass composition is CaO, MgO, and $Na_2O$.

The glass composition may additionally include up to about 30 mol % of fluoride, wherein the fluoride is in the form of: $CaF_2$, NaF, $Na_2PO_3F$, KF, or $SnF_2$.

In other embodiments, the present disclosure provides a glass composition for desensitizing dentin, the glass composition includes from about 50 mol % to about 95 mol % of $B_2O_3$; from about 5 mol % to about 50 mol % of a glass component selected from the group consisting of: $Li_2O$, $Rb_2O$, $K_2O$, $Na_2O$, SrO, CaO, MgO, ZnO and any combination thereof; where the glass composition comprises less than 30 mol % of $Rb_2O$. The glass composition loses at least 5 mass % within 24 hours when exposed to a buffered saline solution, and the glass composition is a particulate material that comprises particles that are from about 1 to about 50 μm in size.

In some examples of the glass compositions, less than 20 mol %, such as less than 15 mol %, less than 10 mol %, or less than 5 mol % of the glass composition is CaO, MgO, and $Na_2O$.

The glass composition may additionally include up to about 30 mol % of fluoride, wherein the fluoride is in the form of: $CaF_2$, NaF, $Na_2PO_3F$, KF, or $SnF_2$.

In other embodiments, the present disclosure provides a glass composition that includes: fluoride, which is provided as from about 5 mol % to about 10 mol % of $CaF_2$, $SnF_2$, NaF, KF, or any combination thereof; and from about 90 mol % to about 95 mol % of a combination of $B_2O_3$, $Na_2O$, MgO, and CaO, where the boron, the magnesium, the combination of Na and any K, and the combination of Ca and any Sn in the glass composition are present in elemental ratios of about 20:about 4:about 6:about 3, respectively.

One example of such a specific glass composition according to the present disclosure includes: about 50 mol % $B_2O_3$, about 15 mol % $Na_2O$, about 20 mol % MgO, about 10 mol % CaO, and about 5 mol % $CaF_2$.

Glass compositions according to the present disclosure may be formulated into a dentin-desensitizing composition, such as a toothpaste, a prophylaxis paste, a tooth varnish, a mouthwash, a dental gel, or a bonding agent. Dentin-desensitizing compositions according to the present disclosure are substantially water-free.

Glass compositions according to the present disclosure may be used for desensitizing dentin, such as in methods that include applying to an individual's dentin: a toothpaste, a prophylaxis paste, a tooth varnish, a mouthwash, a dental gel, or a bonding agent according to the present disclosure.

A glass composition according to the present disclosure may be prepared from a corresponding bulk glass. The chemical formulations are the same between the bulk glass and the particulate material. Another aspect of the present disclosure is a bulk glass having a chemical formulation as disclosed herein.

BRIEF DESCRIPTION OF THE DRAWINGS

Embodiments of the present disclosure will now be described, by way of example only, with reference to the attached Figures.

DETAILED DESCRIPTION

Figure 1:
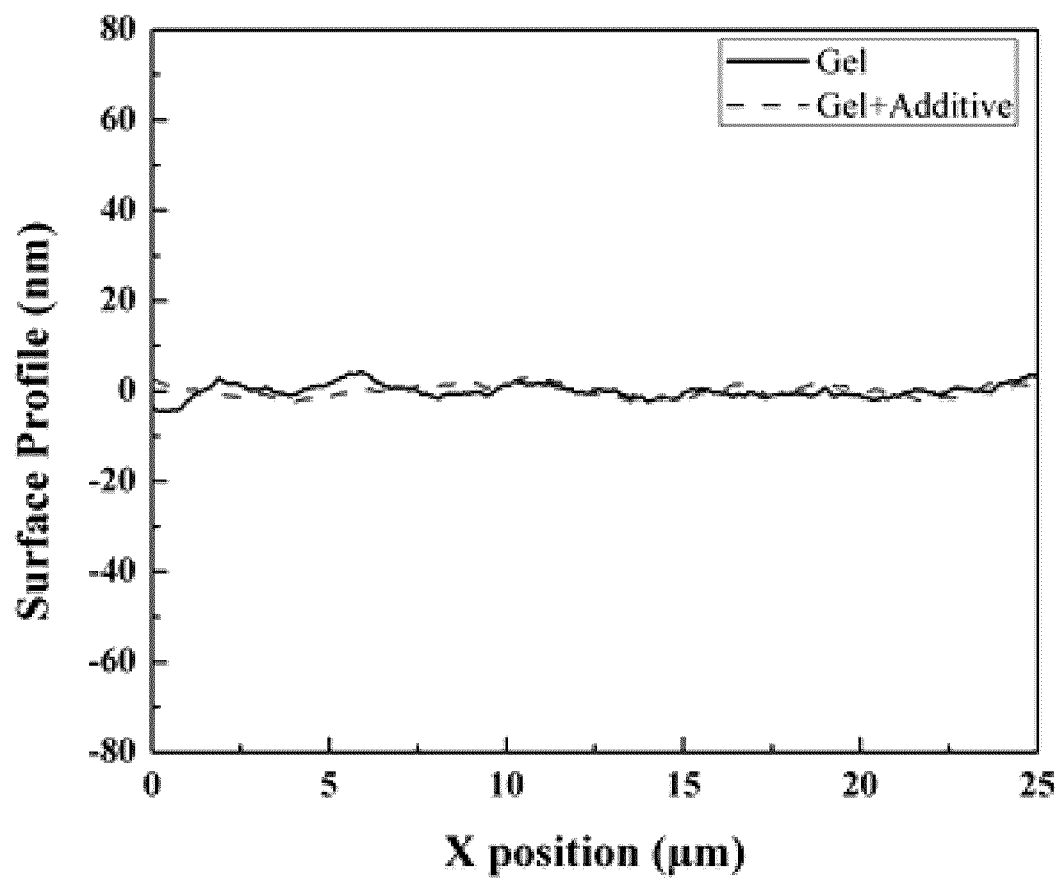
FIG. 1 is an illustration of the average of the surface profile of a resin composite after 20,000 brushing cycles with Gel 7 HT toothpaste ("Gel") vs. Gel 7 HT toothpaste formulated with a glass composition according to the present disclosure ("Gel+Additive").

Glass compositions according to the present disclosure are at least a quaternary system. The glass compositions include from about 50 mol % to about 95 mol % of $B_2O_3$; and from about 5 mol % to about 50 mol % of one or more glass components selected from the group consisting of: $Li_2O$, $Rb_2O$, $K_2O$, $Na_2O$, SrO, CaO, MgO, and ZnO. The glass compositions include less than 30 mol % of $Rb_2O$. Glass compositions according to the present disclosure degrade under physiological conditions, losing at least 5 mass % within 24 hours when exposed to a buffered saline solution.

The glass composition is a particulate material that includes particles that are from about 1 to about 50 μm in size. The glass composition includes at least some particles that are sized to occlude dentinal tubules, thereby desensitizing the dentin. In the context of the present disclosure, a particle sized to occlude a dentinal tubule should be understood to mean that the particle sits in or on top of the dentinal tubule, reducing the movement of the dentinal fluid.

In the context of the present disclosure, a glass composition that is "at least a quaternary system" should be understood to refer to glasses with four or more different elements. For example, a glass composition that is made up of only $B_2O_3$, $Li_2O$ and ZnO would be considered a quaternary system since the glass includes the elements boron, lithium, zinc, and oxygen. Similarly, a glass composition that is made up of only $B_2O_3$, CaO and $CaF_2$ would be considered a quaternary system since the glass includes the elements boron, calcium, fluorine, and oxygen. In contrast, a glass composition that is made up of only $B_2O_3$ and $Na_2O$ would be considered a ternary system since the glass includes the elements boron, sodium, and oxygen.

It should be understood that "about 5 mol % to about 50 mol % of one or more glass components" refers to the total mol % of the glass components, and does not refer to the mol % percent of each individual component. For example, a glass composition according to the present disclosure could include 2.5 mol % of $Li_2O$ and 2.5 mol % of ZnO in order to provide the recited 5 mol % of the additional glass components.

It should be understood that "about X mol %" refers to any value that is within ±2% of the reported percentage. For example, "about 10 mol %" would refer to values from 8 mol % to 12 mol % since all those values would be within ±2% of the reported 10%; and "about 50 mol %" would refer to values from 48 mol % to 52 mol % since all those values would be within ±2% of the reported 50%.

It should be understood that "about X μm" in the context of particle size is determined based on accepted tolerances as per ASTM for a test sieve of the noted size. For example, the accepted tolerance for a 50 μm test sieve is 3 μm. Accordingly, "about 50 μm" refers to particles that are from 47 μm to 53 μm in size. In another example, the accepted tolerance for a 35 μm test sieve is 2.6 μm. Accordingly, "about 35 μm" refers to particles that are from 32.4 μm to 38.6 μm in size. The ASTM accepted tolerance for a 25 μm sieve is 2.2 μm. For test sieves without a standard, accepted tolerance (such as test sieves below 20 μm), the expression "about X μm" refers to ±15% for sizes from 5 to 15 μm, and +50% for sizes less than 5 μm. For example "about 1 μm" refers to particles that are from 0.5 to 1.5 μm in size.

Glass Compositions

Glass compositions according to the present disclosure may include a source of fluoride, such as $CaF_2$, NaF, $Na_2PO_3F$, KF, or $SnF_2$. Including fluoride in the glass composition results in fluoride being released when the glass degrades. The released fluoride may form fluorapatite ($Ca_5(PO_4)_3F$) in or around the dentinal tubules, which may form a protective precipitate and further decrease dentin sensitivity. In a glass composition that includes fluoride the source of fluoride may be up to 30 mol % of the glass composition. In some examples, the source of fluoride may be from about 1 mol % to about 10 mol %, for example from about 1 mol % to about 5 mol %, of the glass composition. In particular examples, the source of fluoride is about 15 mol % of the composition. Compositions that include $CaF_2$ or $SnF_2$ provide twice the amount of fluoride per mole of starting material compared to compositions that use NaF, $Na_2PO_3F$, or KF.

In some examples, the glass composition includes from about 1 mol % to about 10 mol % of fluoride. In some examples, the glass composition includes from about 1 mol % to about 5 mol % of fluoride.

In some examples, glass composition includes sufficient fluoride that 0.1 g of the particulate material releases the fluoride into 10 mL of a buffered saline solution at an average rate of about 1 ppm/hr to about 15 ppm/hr over 1, 2, 4, 8, 12, 18 or 24 hours. In the context of the present disclosure, ppm is measured as mass/mass. In particular examples, the glass composition includes sufficient fluoride that about 4 to about 6 ppm of fluoride is released per hour over 1 hour.

In some examples of glass compositions according to the present disclosure, less than 20 mol %, such as less than 15 mol %, less than 10 mol %, or less than 5 mol % of the glass composition is CaO, MgO, and $Na_2O$.

In an example of a glass composition according to the present disclosure, the glass composition does not include any CuO; and includes less than 0.1 mol % of BaO, and less than 0.1 mol % of $P_2O_5$. In particular examples, the glass composition does not include any CuO, BaO, or $P_2O_5$.

A glass composition according to the present disclosure may include from about 5 mol % to about 50 mol % of one or more glass components selected from the group consisting of: $Li_2O$, $Rb_2O$, $K_2O$, $Na_2O$, SrO, and ZnO; and wherein the glass composition comprises less than 0.1 mol % of CaO and less than 0.1 mol % of MgO.

A glass composition according to the present disclosure may include from about 5 mol % to about 50 mol % of one or more glass components selected from the group consisting of: $Li_2O$, $Rb_2O$, $K_2O$, SrO, and ZnO; and wherein the glass composition comprises less than 0.1 mol % of CaO, less than 0.1 mol % of MgO, and less than 0.1 mol % of $Na_2O$.

A glass composition according to the present disclosure may include from about 50 mol % to about 80 mol % of $B_2O_3$, such as about 50 mol % of $B_2O_3$.

A glass composition according to the present disclosure may include about 5 mol % to about 40 mol %, such as from about 20 mol % to about 40 mol %, of the one or more glass components selected from the group consisting of: $Li_2O$, $Rb_2O$, $K_2O$, $Na_2O$, SrO, CaO, MgO, and ZnO.

A glass composition according to the present disclosure may include $B_2O_3$, $Li_2O$, and ZnO, and optionally $Rb_2O$, $Na_2O$, and/or a source of fluoride. In particular examples, the glass composition includes: from about 5 mol % to about 25 mol % $Li_2O$, and from about 5 mol % to about 25 mol % $Rb_2O$; or from about 5 mol % to about 25 mol % $Li_2O$, and from about 5 mol % to about 15 mol % ZnO, and optionally from about 5 mol % to about 15 mol % of $Na_2O$. The glass compositions may include about 50 mol % of $B_2O_3$, or about 70 mol % $B_2O_3$.

A glass composition according to the present disclosure may include $B_2O_3$, and ZnO, and optionally $Rb_2O$ and/or a source of fluoride. In particular examples, the glass composition includes: from about 5 mol % to about 30 mol % ZnO. If present, the $RbO_2$ may be included in an amount from about 5 mol % to about 30 mol %. The glass compositions may include about 50 mol % of $B_2O_3$.

A glass composition according to the present disclosure may include $B_2O_3$, and SrO, and optionally ZnO and/or a source of fluoride. In particular examples, the glass composition includes: from about 5 mol % to about 30 mol % SrO. If present, the ZnO may be included in an amount from about 5 mol % to about 30 mol %. The glass compositions may include about 50 mol % of $B_2O_3$.

As noted above, the present disclosure also provides a glass composition that includes: fluoride, which is provided as from about 5 mol % to about 10 mol % of $CaF_2$, $SnF_2$, NaF, KF, or any combination thereof; and from about 90 mol % to about 95 mol % of a combination of $B_2O_3$, $Na_2O$, MgO, and CaO, where the boron, the magnesium, the combination of Na and any K, and the combination of Ca and any Sn in the glass composition are present in elemental ratios of about 20:about 4:about 6:about 3, respectively.

One specific example of such a glass composition includes: about 50 mol % $B_2O_3$, about 15 mol % $Na_2O$, about 20 mol % MgO, about 10 mol % CaO, and about 5 mol % $CaF_2$. This composition may be referred to herein as composition "PBF1".

Another specific example of such a glass composition includes: about 48 mol % $B_2O_3$, about 9 mol % $Na_2O$, about 19 mol % MgO, about 14 mol % CaO, and about 10 mol % NaF. This composition may be referred to herein as composition "PBF1-Na".

Particle Size Distribution

A glass composition according to the present disclosure is a particulate material that includes particles that are from about 1 to about 50 μm in size. At least some of the particles are sized to sit in or on top of a dentinal tubule. Dentinal tubules have a natural variation in diameter and are primarily from about 0.5 to about 8 μm in size, for example, from about 0.5 to about 5 μm in size. Accordingly, glass compositions of the present disclosure may be used for desensitizing dentin, which may temporarily reduce pain associated with sensitive teeth.

In some examples, at least 75% of the particles making up the particulate material are smaller than 50 μm in size. In other examples, at least 85% or at least 95% of the particles are smaller than 50 μm in size. In some examples, at least 5% of the particles making up the particulate material are smaller than 7 μm in size.

In particular examples, the particulate material is made up of a plurality of particles where at least 5% of the particles are smaller than 35 μm in size, at least 5% of the particles are smaller than 15 µm in size, and at least 5% of the particles are smaller than 7 µm in size.

In particular examples, the particulate material is made up of a plurality of particles where at least 5% of the particles are from about 15 µm to about 35 µm in size, at least 5% of the particles are from about 6 µm to about 15 µm in size, and at least 5% of the particles are from about 3 µm to about 7 µm in size.

In some particular examples, the particulate material is made up of a plurality of particles where the particle size distribution is Dx10 of about 5 um, Dx50 of about 15 um, and Dx90 of about 30 um.

Degradation

Glass compositions according to the present disclosure degrade under physiological conditions, losing at least 5 mass % within 24 hours when exposed to a buffered saline solution. In some examples, the glass composition may lose at least 20 mass %, at least 40 mass %, at least 60 mass %, or at least 80 mass % within 24 hours when exposed to the buffered saline solution.

Dentin-Desensitizing Compositions

Glass compositions according to the present disclosure may be formulated in a dentin-desensitizing composition that includes a water-free, orally-compatible carrier. Dentin-desensitizing compositions according to the present disclosure are free of water since the glass composition degrades if exposed to water.

In the context of the present disclosure, "water-free" should be understood to mean that the dentin-desensitizing composition includes so little water that the glass composition remains capable of reducing dentin sensitivity over the expected lifespan of the product. The expected lifespan of the product refers to the longest expected time between when the dentin-desensitizing composition was produced and when the dentin-desensitizing composition was completely used up or disposed of.

The orally-compatible carrier used in the dentin-desensitizing composition may be a mouthwash, a carrier formulated to mix with additional components to form a mouthwash, or an orally-compatible viscous carrier, such as a toothpaste, a dental gel, a prophylaxis paste, a tooth varnish, a bonding agent, or a carrier that is formulated to mix with additional components to form a toothpaste. The orally-compatible viscous carrier may have a viscosity from about 100 cP at 30° C. to about 150,000 cp at 30° C.

The dentin-desensitizing composition may include a glass composition according to the present disclosure that includes fluoride, as discussed above, where the glass composition is present in a sufficient amount that the desensitizing composition includes about 100 ppm to about 5,000 ppm of the fluoride.

One example of a dentin-desensitizing composition according to the present disclosure is a toothpaste that includes a glass composition according to the present disclosure and: an abrasive; a detergent such as sodium lauryl sulfate; a fluoride source; an antibacterial agent; a flavorant; a remineralizer; a sugar alcohol such as glycerol, sorbitol, or xylitol; another dentin desensitizing agent; a hydrophilic polymer such as polyethylene glycol; or any combination thereof. The glass composition may be from about 0.5 to about 15 mass % of the toothpaste.

One particular example of a dentin-desensitizing composition according to the present disclosure is a toothpaste that includes a glass composition according to the present disclosure and: glycerin, silica, a polyethylene glycol (such as PEG 400), titanium dioxide, a carbomer, and a sweetener (such as potassium acesulfame or sodium saccharin).

Another particular example of a dentin-desensitizing composition according to the present disclosure is a toothpaste that includes a glass composition according to the present disclosure and: α-carbomer, DL-limonene, glycerin, mint flavor, a polyethylene glycol (such as PEG-8), silica, titanium dioxide, sodium lauryl sulphate, and a sweetener (such as potassium acesulfame or sodium saccharin).

Another example of a dentin-desensitizing composition according to the present disclosure is a carrier that includes a glass composition according to the present disclosure, where the carrier is formulated to be mixed with additional components to form a toothpaste.

Yet another example of a dentin-desensitizing composition according to the present disclosure is a carrier formulated to mix with additional components to form a mouthwash. Particular examples of the carrier include a glass composition according to the present disclosure and: a water-free alcohol, cetylpyridinium chloride, chlorhexidine, an essential oil, benzoic acid, a poloxamer, sodium benzoate, a flavor, a coloring, or any combination thereof. The additional component(s) that is/are mixed with the carrier to form the mouthwash may include: water, peroxide, cetylpyridinium chloride, chlorhexidine, an essential oil, alcohol, benzoic acid, a poloxamer, sodium benzoate, a flavouring, a colouring, or any combination thereof. The carrier and the additional components may be kept in separate compartments, and mixed together before the mixture is used as a mouthwash. The separate compartments may be in the form of a multi-chambered bottle, such as a bifurcated bottle.

Another example of a dentin-desensitizing composition according to the present disclosure is a prophylaxis paste (also referred to as a "prophy paste") that includes a glass composition according to the present disclosure. Particular examples of contemplated prophy pastes include a glass composition according to the present disclosure and: pumice, glycerin, diatomite (preferably fine grit), sodium silicate, methyl salicylate, monosodium phosphate, sodium carboxymethylcellulose, a sweetener (such as potassium acesulfame or sodium saccharin), a flavouring, a colouring, or any combination thereof.

Methods

Glass compositions according to the present disclosure may be synthesized by: mixing appropriate molar amounts of the starting reagents; packing the precursor blend in a platinum crucible (Johnson Matthey, Noble Metals, Pennsylvania); placing the packed crucible in a furnace (Carbolite, RHF 1600) at room temperature; heating the furnace (such as at a rate of 25° C./minute) to an initial dwelling temperature of 600° C.; holding the temperature for 60 minutes; ramping the temperature (such as at a rate of 20° C./minute) to a dwelling temperature of 1,100° C.; holding the temperature for 60 minutes; and quenching the glass melt between two stainless steel plates.

It should be understood that the specific ramp rate, times, and temperatures disclosed above could be modified, so long as the glass melts. Ramp rates from 10-20 degrees/min, and holding at the dwell temperature may remove at least some gas bubbles from the glass.

The resulting quenched glasses may be ground/milled separately within a planetary micro mill (Pulverisette 7, Fritsch, Germany) and sieved with ASTM E-11 compliant sieves (Cole Palmer, U.S.A) to obtain particles of <25 µm. Glasses may be stored under vacuum in glass scintillation vials.

Although the resulting glass composition includes oxides, the starting reagents may include oxides, carbonates, or both. For example, the starting reagent may include boron oxide, rubidium carbonate, lithium carbonate, and calcium fluoride. The rubidium carbonate and lithium carbonate decompose in the furnace to release $CO_2$, generating their corresponding oxides.

Particle size is measured using a Malvern Mastersizer (MS) 3000 laser diffraction particle size analyzer. Glass powders are separately suspended in deionized water to obtain an obscuration value for the suspension between 5-8%. Suspensions are measured using both a blue (A=470 nm) and red (A=632.8 nm) laser and are measured 5 times (n=5).

Fluoride release is measured by placing 0.1 g of the glass composition in 10 ml of TRIS buffered saline (BioUltra, Sigma Aldrich, Canada) in a 15 ml Falcon tube. The solution is agitated at 120 rpm and kept at a temperature of 37° C. for the desired release period, such as for 1, 3, 6, 12 or 24 h. On completion, the liquid portion is decanted and filtered using a 0.22 µm filter (Sarstedt syringe filter, Canada) into new clean 15 ml Falcon tubes, which were capped and then stored at 4° C. until the amount of fluoride is quantified. The concentration of the released fluoride is quantified using an Accumet®AB250 pH/ion selective electrode meter equipped with electrode fluoride combination (Accumet®). Standard solutions are prepared using a fluoride analytical standard specifically for ion selective electrodes (NaF, 0.1 M F, Sigma Aldrich, Canada) and calibration cures are retrieved before analysis. Liquid extracts derived from the extraction of each composition were prepared for ion analysis as per the electrode manufactures instructions. The ion concentrations are reported as the average of n=3±SD.

In the context of the present disclosure, mass loss of a glass composition is in relation to a solid glass cylinder that is 6 mm in length and 4 mm in diameter. The glass cylinder is prepared by producing molten glass, as described above, quenching the molten glass in a stainless steel mould (6 mm in length by 4 mm in diameter), set between two stainless steel plates. The excess glass on the cylinders is carefully etched off by a Speedy Sharp utensil and the remainder of the excess glass is removed (while placed back into the stainless steel moulds) using a grinding/polishing wheel with 240 sand paper and applying pressure to the moulds/glass on the wheel. Glass cylinders with uneven edges, air bubbles, or chips are excluded.

The mass loss for a given glass composition is measured using three cylinders. The length and diameter of each cylinder is measured and recorded 3 times (changing the position of measurement each time) and recorded as an average±SD. The mass of each cylinder is measured separately (Sartorius Cubis, Model MSU-224S 100 DI, Cole Palmer). The three cylinders are placed in separate 50 mL falcon tubes with 20 mL of TRIS buffered saline (BioUltra, Sigma Aldrich, Canada) in each tube. The tubes are then placed in a shaking incubator (Thermos Scientific, MaxQ 4000) at 37° C. and agitated at 120 rpm for 24 hrs. After the 24 hours, the cylinders are filtered from the solution, rinsed with cold distilled $H_2O$, and placed to dry overnight in a 37° C. oven. Once dry, the length, diameter and mass are measured.

Abrasiveness of a composition is determined by measuring the gloss and surface roughness of a resin composite or an enamel surface after brushing with the composition. ESPE Filtek Supreme Ultra Universal Restorative, shade A2B (3M, St. Paul, Minnesota, USA), is cured in a 12.7 mm diameter, 2 mm thick metal split-mold. Mylar sheets are placed above and below the mold and glass plates are used to press the composite flat and squeeze out any extra material. A broadband multiwave LED light curing unit (Valo Grand, Ultradent Products, South Jordan, Utah, USA) is placed directly on top of the specimens and cured for 20 s at the standard setting. Excess material is removed by hand before mounting the specimens for brushing.

Samples are stored at 37° C. in the dark for a minimum of 24 h before use. The surface of the enamel specimens are prepared by polishing with varying levels of grit to produce a flat and smooth surface. Low grit sandpaper is used to create the initial flat surface (P800C, Klingspor, Haiger, Germany) and then increasing amounts of grit are used, followed by polishing. The final polishing steps are carried out on cloth pads with 3 µm and then 0.3 µm alumina oxide powder slurries (Buehler Ltd., Lake Bluff, Illinois, USA). Each polishing step is carried out for approximately 1 min with pressure applied by hand.

A custom-built brushing machine (Ultradent, South Jordan, UT, USA) simulates toothbrushing of 10 samples simultaneously. It is equipped with toothbrushes (GUM brand 459PC, Sunstar, Guelph, Ontario, Canada) with constant loads of 176 g applied during brushing. The toothbrushes are replaced after 10,000 brushing cycles. The samples are covered with a minimum of 3 mm of a 5:8 weight ratio toothpaste slurry with distilled water during brushing. Samples are rotated to a different position every 2,500 brush cycles (ensuring that the sample was brushed with the same toothpaste each time it was moved). 20,000 brush cycles represent approximately 2 years of brushing. The repetitions and position of the toothpastes in the machine are randomized with a random number generator (for each substrate material), while manually assuring there was a minimum of two repeats of the same toothpaste during a single run to ensure rotation of toothbrushes.

A glossmeter (Novo-Curve G, Rhopoint Instruments, Hastings, UK) is used to measure the gloss of the composite and enamel surfaces. The gloss is measured in three random points to create an average for the surface. The glossmeter calibration is verified each day using a traceable calibration tile with high and low reflectivity. The gloss is measured at 0, 5,000, 10,000, 15,000 and 20,000 brush cycles and new toothpaste slurry is used after measuring the gloss.

The average roughness of the surfaces is also measured before brushing and after 20,000 brushing cycles. An atomic force microscope (nGauge, ICSPI Corporation, Rev. 1.0, Waterloo, Ontario, Canada) is used to measure the average roughness at 3 different positions to form an average of the surface. A 25×25 µm area is scanned at a rate of 1200 µs/pixel. The data is analyzed using Gwyddion (http://gwyddion.net) software.

EXAMPLES

The glass compositions shown in Table 1 were all synthesized by: weighing determined amounts of the analytical grade reagents (boron oxide, rubidium carbonate, lithium carbonate, and calcium fluoride) (Sigma Aldrich, Canada). The individual formulations were mixed for 60 mins to ensure homogeneity. Each precursor blend was placed and packed in 50 mL platinum crucibles (Johnson Matthey, Noble Metals, Pennsylvania). The pack crucible was then placed in a furnace (Carbolite, RHF 1600) at room temperature. The furnace was heated (25° C./minute) to an initial dwelling temperature of 600° C. and held for 60 minutes. The temperature was then ramped (20° C./minute) to a final dwelling temperature of 1,100° C. and held for 60 minutes.

On removal, each glass melt was quenched between two stainless steel plates. The resulting quenched glasses were ground/milled separately within a planetary micro mill (Pulverisette 7, Fritsch, Germany) and sieved with ASTM E-11 compliant sieves (Cole Palmer, U.S.A) to obtain particles of <25 μm.

TABLE 1

Exemplary glass compositions according to the present disclosure

| Glass Identifier | $B_2O_3$ (mol %) | $Li_2O$ (mol %) | $Rb_2O$ (mol %) | $CaF_2$ (mol %) |
|---|---|---|---|---|
| BCF100 | 70 | 20 | 10 | 0 |
| BCF101 | 70 | 20 | 9 | 1 |
| BCF102 | 70 | 20 | 8 | 2 |
| BCF103 | 70 | 20 | 7 | 3 |
| BCF104 | 70 | 20 | 6 | 4 |
| BCF200 | 70 | 10 | 20 | 0 |
| BCF201 | 70 | 9 | 20 | 1 |
| BCF202 | 70 | 8 | 20 | 2 |
| BCF203 | 70 | 7 | 20 | 3 |
| BCF204 | 70 | 6 | 20 | 4 |

The particle size distribution for the exemplary glasses of Table 1 is shown in Table 2.

TABLE 2

Particle size distribution (μm).

| Glass Identifier | Dx (10) | Dx (50) | Dx (90) |
|---|---|---|---|
| BCF100 | 5.16 | 14.5 | 29.7 |
| BCF101 | 4.23 | 11.9 | 25 |
| BCF102 | 4.77 | 13.8 | 29.1 |
| BCF103 | 4.75 | 13.6 | 28.4 |
| BCF104 | 3.97 | 12.7 | 28.3 |
| BCF200 | 6.87 | 15.1 | 27.6 |
| BCF201 | 6.31 | 16.2 | 31.7 |
| BCF202 | 6.5 | 16.9 | 32.5 |
| BCF203 | 6.22 | 16.5 | 32.4 |
| BCF204 | 6.35 | 17 | 33.6 |

It should be understood that where "Dx(#)" refers to #% of particles that are smaller in size than the noted value. For example, BCF100 has a Dx(10) of 5.16 microns, which means that 10% of the particles are less than 5.16 microns in size.

The particles of the exemplary glasses of Table 1 were evaluated for fluoride release in a buffered saline solution over 12 and 24 hours using the method discuss above. The ppm values of released fluoride are shown in Table 3.

TABLE 3

Mean fluoride release (ppm) at 12 and 24 hours.

| Glass Identifier | Fluoride release- 12 hours (ppm) | Fluoride release- 24 hours (ppm) |
|---|---|---|
| BCF100 | 0 | 0 |
| BCF101 | 32 | 31 |
| BCF102 | 59 | 58 |
| BCF103 | 69 | 77 |
| BCF104 | 65 | 70 |
| BCF200 | 0 | 0 |
| BCF201 | 24 | 23 |
| BCF202 | 48 | 47 |
| BCF203 | 62 | 59 |
| BCF204 | 76 | 71 |

BCF201 was formulated into two toothpastes to test the abrasive effects of the glass particles, and compared to the abrasive effects of Sensodyne™ Whitening Repair and Protect™ toothpaste ("Sensodyne"), and Colgate™ Optic White™ toothpaste ("Colgate Optic"). The exemplary glass was formulated with: (a) Colgate™ Enamel Health Sensitivity Relief™ (Colgate-Palmolive, Toronto, ON, Canada) ("Colgate EN"), or (b) Gel 7 HT (Germiphene, Brantford, ON, Canada) ("Gel"), a neutral pH fluoride gel dentifrice that does not contain any abrasive materials.

Figure 2:
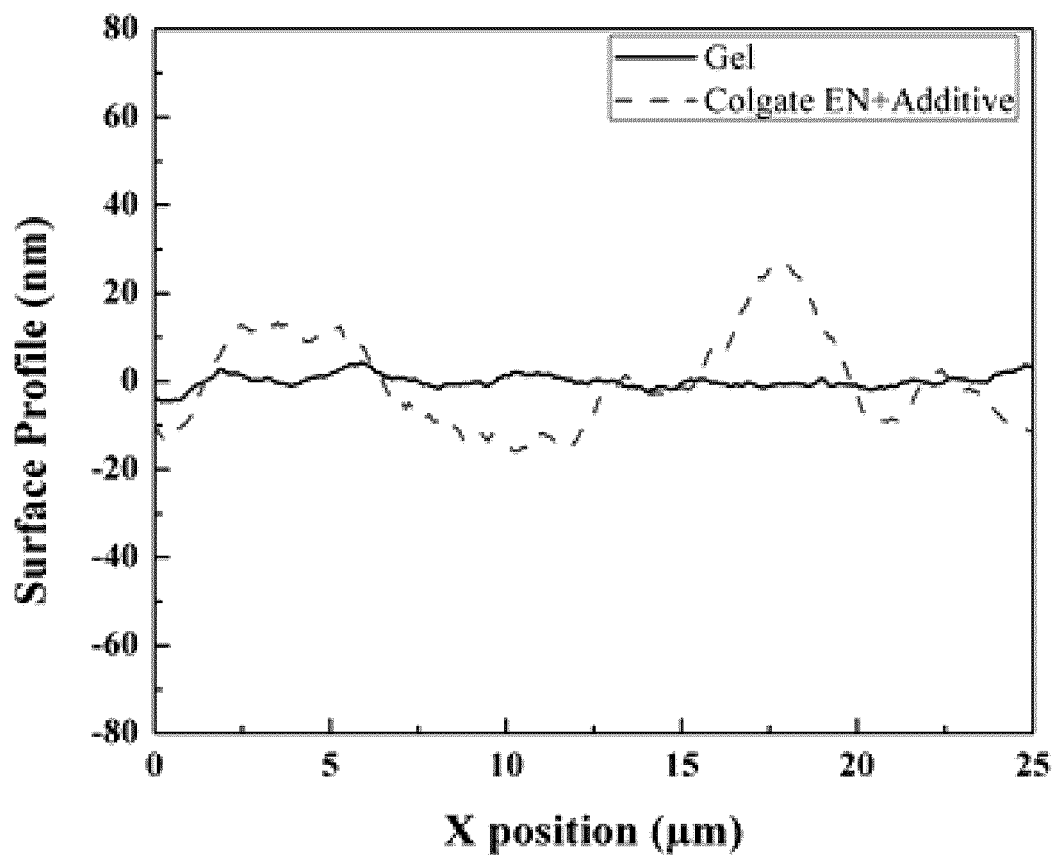
FIG. 2 is an illustration of the average of the surface profile of a resin composite after 20,000 brushing cycles with Gel 7 HT ("Gel") toothpaste vs. Colgate™ Enamel Health Sensitivity Relief™ toothpaste formulated with the glass composition ("Colgate EN+Additive").
Figure 3:
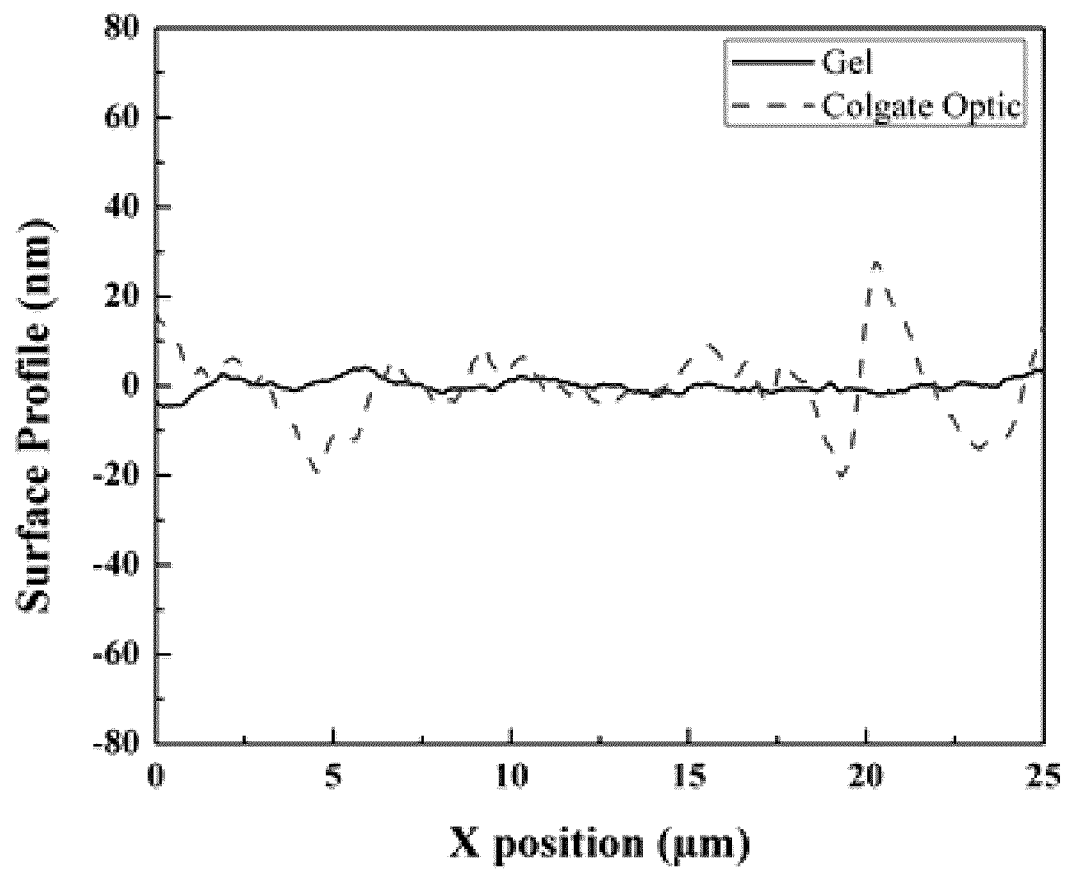
FIG. 3 is an illustration of the average of the surface profile of a resin composite after 20,000 brushing cycles with Gel 7 HT toothpaste ("Gel") vs. Colgate™ Optic White™ toothpaste ("Colgate Optic").
Figure 4:
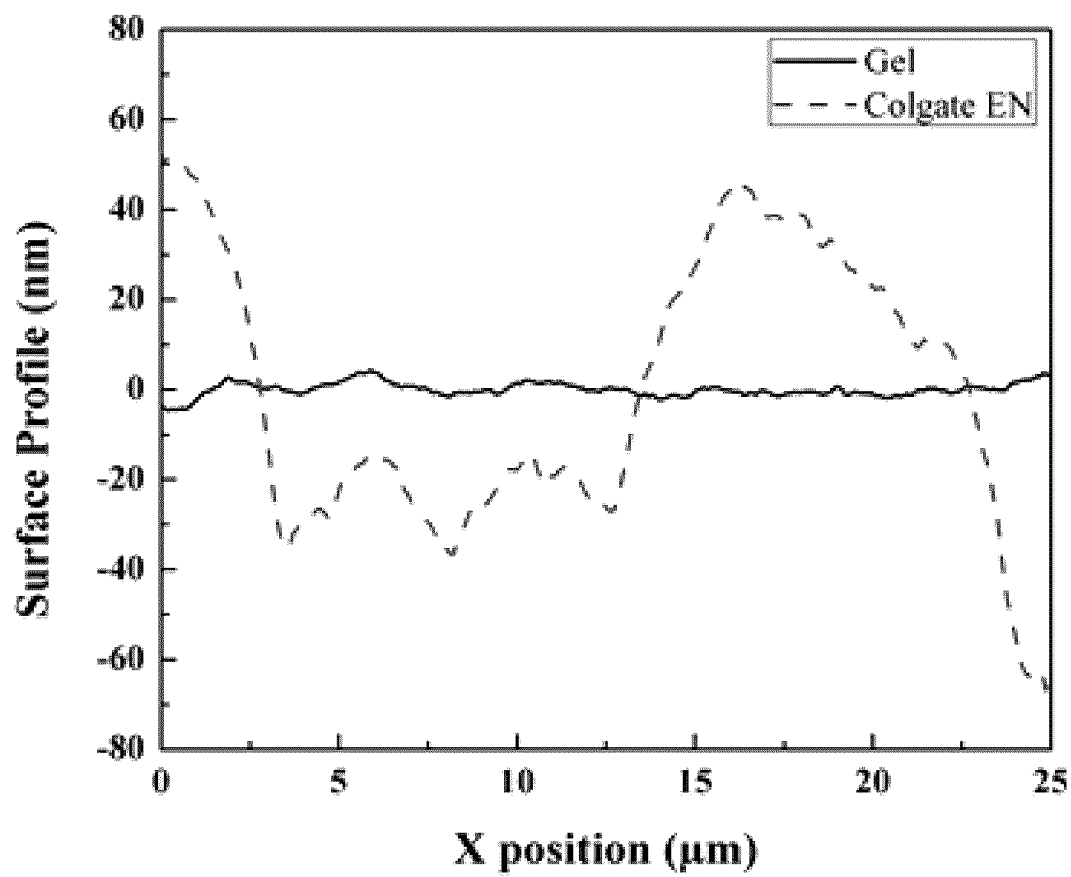
FIG. 4 is an illustration of the average of the surface profile of a resin composite after 20,000 brushing cycles with Gel 7 HT ("Gel") toothpaste vs. Colgate™ Enamel Health Sensitivity Relief™ toothpaste ("Colgate EN").
Figure 5:
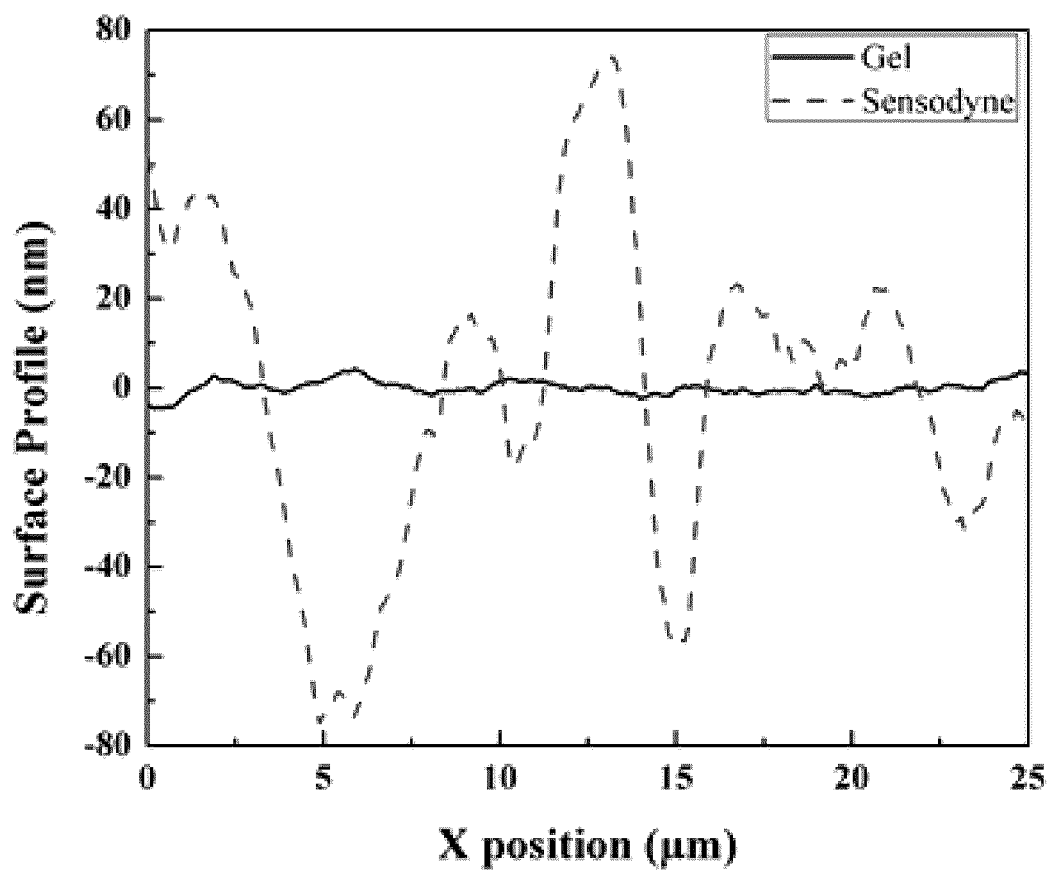
FIG. 5 is an illustration of the average of the surface profile of a resin composite after 20,000 brushing cycles with Gel 7 HT toothpaste ("Gel") vs. Sensodyne™ Whitening Repair and Protect™ toothpaste ("Sensodyne").
Figure 6:
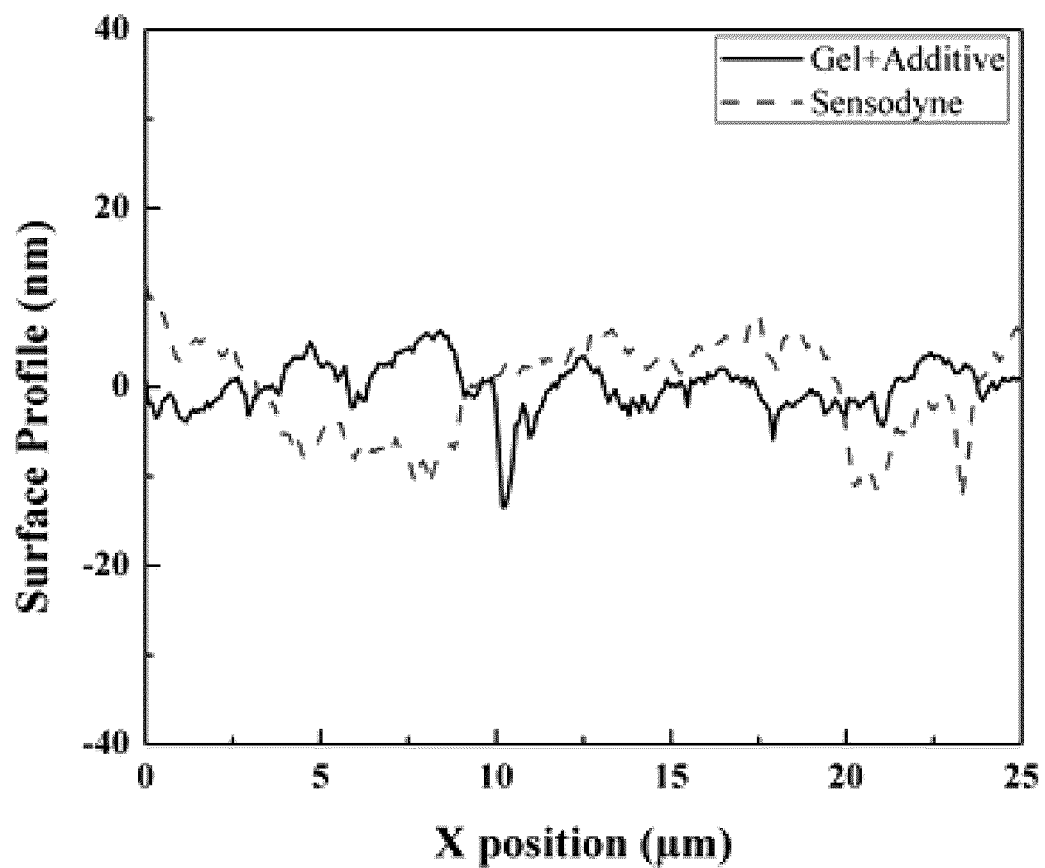
FIG. 6 is an illustration of the average of the surface profile of an enamel surface after 20,000 brushing cycles with Gel 7 HT toothpaste formulated with the glass composition ("Gel+Additive") vs. Sensodyne™ Whitening Repair and Protect™ toothpaste ("Sensodyne").
Figure 7:
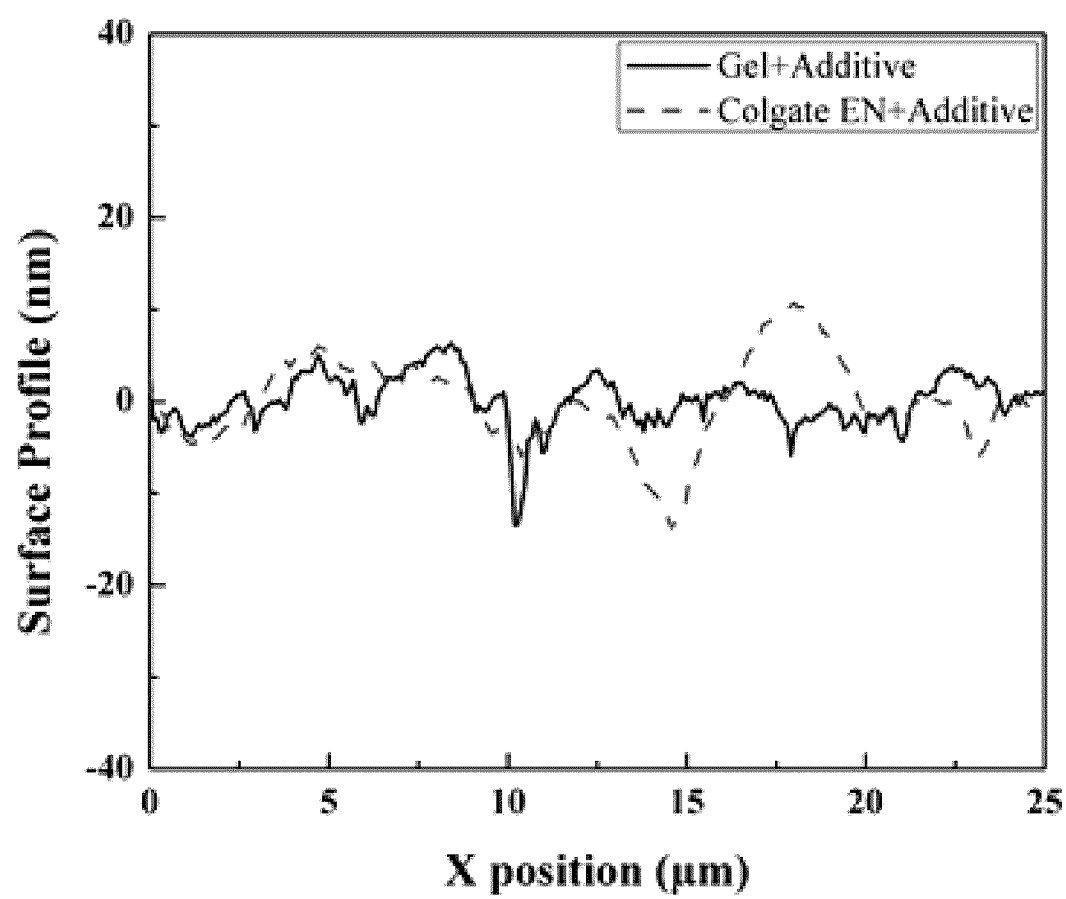
FIG. 7 is an illustration of the average of the surface profile of an enamel surface after 20,000 brushing cycles with Gel 7 HT toothpaste formulated with the glass composition ("Gel+Additive") vs. Colgate™ Enamel Health Sensitivity Relief™ toothpaste formulated with the glass composition ("Colgate EN+Additive").
Figure 8:
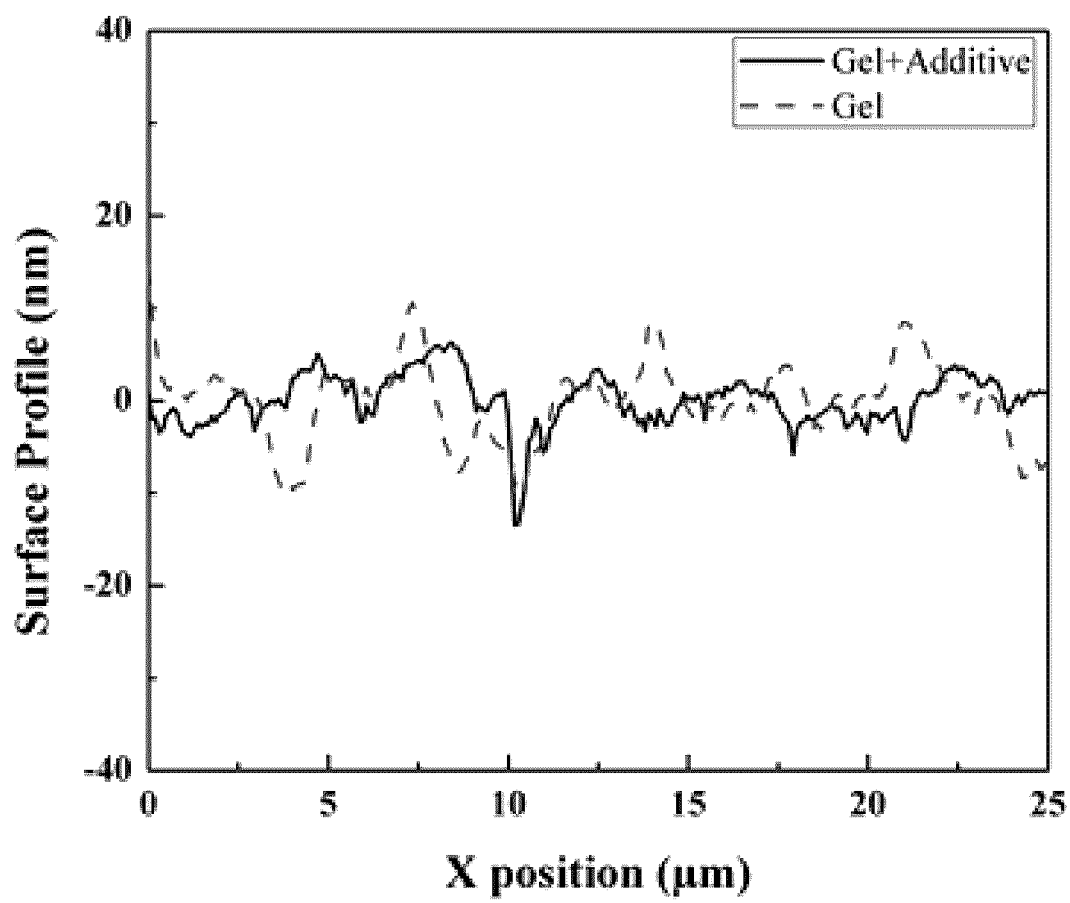
FIG. 8 is an illustration of the average of the surface profile of an enamel surface after 20,000 brushing cycles with Gel 7 HT toothpaste ("Gel") vs. Gel 7 HT toothpaste formulated with the glass composition ("Gel+Additive").
Figure 9:
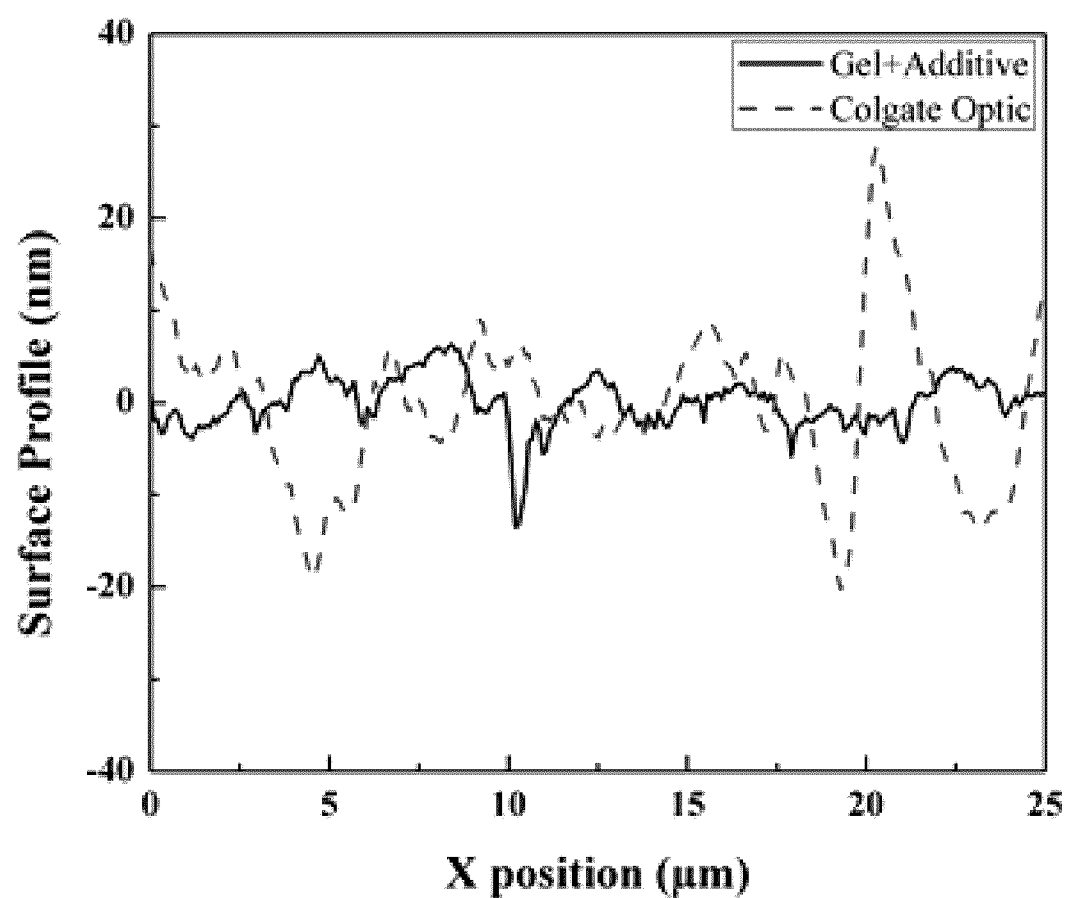
FIG. 9 is an illustration of the average of the surface profile of an enamel surface after 20,000 brushing cycles with Gel 7 HT toothpaste formulated with the glass composition ("Gel+Additive") vs. Colgate™ Optic White™ toothpaste ("Colgate Optic").
Figure 10:
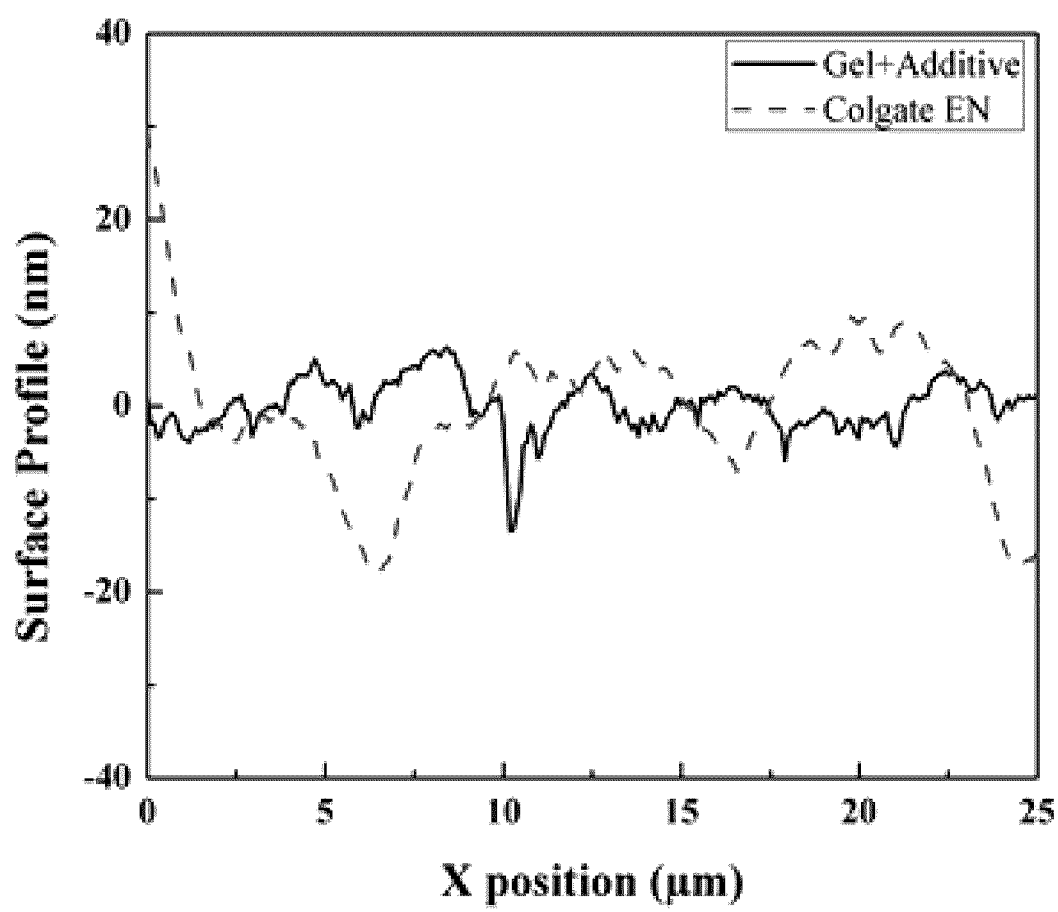
FIG. 10 is an illustration of the average of the surface profile of an enamel surface after 20,000 brushing cycles with Gel 7 HT toothpaste formulated with the glass composition ("Gel+Additive") vs. Colgate™ Enamel Health Sensitivity Relief™ toothpaste ("Colgate EN").

The results of the abrasive tests are illustrated the following tables, and in FIGS. 1 to 10. Table 4 shows the Gloss Units of a resin composite surface after different numbers of brushing cycles using the different toothpastes. Table 5 shows the Gloss Units of a resin composite after different numbers of brushing cycles using the different toothpastes. Table 6 shows the roughness of a resin composite surface after 20,000 brushing cycles using the different toothpastes. Table 7 shows the roughness of an enamel surface after 20,000 brushing cycles using the different toothpastes.

TABLE 4

Gloss Units of a resin composite surface after different numbers of brushing cycles

| Brushing cycles | Gel | Gel + BCF201 | Colgate EN | Colgate EN + BCF201 | Colgate Optic | Sensodyne |
|---|---|---|---|---|---|---|
| 0 | 91 +/− 3 | 91 +/− 3 | 90 +/− 3 | 90 +/− 3 | 90 +/− 3 | 91 +/− 3 |
| 5,000 | 91 +/− 4 | 91 +/− 3 | 63 +/− 9 | 69 +/− 8 | 75 +/− 6 | 56 +/− 8 |
| 10,000 | 90 +/− 3 | 91 +/− 3 | 55 +/− 1 | 64 +/− 10 | 68 +/− 8 | 46 +/− 9 |
| 15,000 | 90 +/− 3 | 91 +/− 3 | 49 +/− 7 | 59 +/− 9 | 62 +/− 8 | 39 +/− 8 |
| 20,000 | 89 +/− 4 | 90 +/− 3 | 46 +/− 6 | 52 +/− 8 | 56 +/− 10 | 25 +/− 7 |

TABLE 5

Gloss Units of an enamel surface after different numbers of brushing cycles

| Brushing cycles | Gel | Gel + BCF201 | Colgate EN | Colgate EN + BCF201 | Colgate Optic | Sensodyne |
|---|---|---|---|---|---|---|
| 0 | 105 +/− 5 | 105 +/− 4 | 105 +/− 3 | 105 +/− 4 | 105 +/− 3 | 105 +/− 3 |
| 5,000 | 83 +/− 5 | 103 +/− 3 | 96 +/− 9 | 103 +/− 5 | 93 +/− 5 | 103 +/− 4 |
| 10,000 | 73 +/− 7 | 100 +/− 4 | 89 +/− 10 | 102 +/− 3 | 86 +/− 6 | 102 +/− 5 |
| 15,000 | 68 +/− 5 | 100 +/− 4 | 85 +/− 10 | 101 +/− 4 | 80 +/− 4 | 102 +/− 3 |
| 20,000 | 60 +/− 8 | 100 +/− 3 | 79 +/− 11 | 99 +/− 4 | 76 +/− 4 | 100 +/− 4 |

TABLE 6

Roughness of a resin composite surface after 20,000 brushing cycles

| Brushing cycles | Gel | Gel + BCF201 | Colgate EN | Colgate EN + BCF201 | Colgate Optic | Sensodyne |
|---|---|---|---|---|---|---|
| 0 | 7 +/− 2[a,b] | 7 +/− 3[a,b] | 8 +/− 2[a,b] | 9 +/− 4[a] | 9 +/− 3[a] | 9 +/− 3[a] |
| 20,000 | 4 +/− 1[b] | 6 +/− 2[a,b] | 42 +/− 9 | 30 +/− 9 | 35 +/− 13 | 65 +/− 22 |

TABLE 7

Roughness of an enamel surface after 20,000 brushing cycles

| Brushing cycles | Gel | Gel + BCF201 | Colgate EN | Colgate EN + BCF201 | Colgate Optic | Sensodyne |
|---|---|---|---|---|---|---|
| 0 | 5 +/− 2[c] | 5 +/− 1[c] | 6 +/− 2[c] | 10 +/− 10[c,d] | 5 +/− 1[c] | 6 +/− 3[c] |
| 20,000 | 5 +/− 2[c] | 5 +/− 1[c] | 20 +/− 12[c] | 9 +/− 5[d] | 19 +/− 5[e] | 8 +/− 3[c,d] |

Additional exemplary glass compositions according to the present disclosure are shown in Table 8, along with glass compositions that are not examples of the present disclosure, which shows the mole percentages of different components.

TABLE 8

| Glass Identifier | $B_2O_3$ | $Li_2O$ | $RbO_2$ | $Na_2O$ | SrO | ZnO | $CaF_2$ | NaF | KF | $SnF_2$ |
|---|---|---|---|---|---|---|---|---|---|---|
| BCF301 | 50.0 | 23.2 | 0.0 | 0.0 | 0.0 | 0.0 | 26.8 | 0.0 | 0.0 | 0.0 |
| BCF302 | 50.0 | 0.0 | 0.0 | 0.0 | 0.0 | 0.0 | 50.0 | 0.0 | 0.0 | 0.0 |
| BCF303 | 50.0 | 0.0 | 0.0 | 0.0 | 0.0 | 0.0 | 0.0 | 0.0 | 24.4 | 25.6 |
| BCF304 | 50.0 | 0.0 | 0.0 | 0.0 | 0.0 | 0.0 | 0.0 | 24.2 | 0.0 | 25.8 |
| BCF305 | 50.0 | 23.8 | 0.0 | 0.0 | 0.0 | 0.0 | 0.0 | 0.0 | 0.0 | 26.2 |
| BCF306 | 50.0 | 0.0 | 0.0 | 0.0 | 24.5 | 0.0 | 0.0 | 0.0 | 0.0 | 25.5 |
| BCF307 | 50.0 | 0.0 | 0.0 | 0.0 | 0.0 | 0.0 | 25.1 | 0.0 | 24.9 | 0.0 |
| BCF308 | 50.0 | 0.0 | 0.0 | 0.0 | 0.0 | 24.3 | 0.0 | 0.0 | 25.7 | 0.0 |
| BCF309 | 50.0 | 0.0 | 0.0 | 0.0 | 0.0 | 0.0 | 0.0 | 0.0 | 0.0 | 50.0 |
| BCF310 | 71.2 | 0.0 | 0.0 | 0.0 | 0.0 | 0.0 | 0.0 | 0.0 | 28.8 | 0.0 |
| BCF311 | 50.0 | 0.0 | 0.0 | 24.2 | 0.0 | 0.0 | 0.0 | 0.0 | 0.0 | 25.8 |
| BCF312 | 50.0 | 25.4 | 0.0 | 0.0 | 0.0 | 0.0 | 0.0 | 0.0 | 24.6 | 0.0 |
| BCF313 | 50.0 | 25.0 | 0.0 | 0.0 | 25.0 | 0.0 | 0.0 | 0.0 | 0.0 | 0.0 |
| BCF314 | 50.0 | 24.2 | 25.8 | 0.0 | 0.0 | 0.0 | 0.0 | 0.0 | 0.0 | 0.0 |
| BCF315 | 50.0 | 0.0 | 0.0 | 0.0 | 0.0 | 0.0 | 50.0 | 0.0 | 0.0 | 0.0 |
| BCF316 | 74.2 | 0.0 | 0.0 | 0.0 | 0.0 | 0.0 | 0.0 | 25.8 | 0.0 | 0.0 |
| BCF317 | 50.0 | 0.0 | 0.0 | 0.0 | 0.0 | 0.0 | 25.7 | 24.3 | 0.0 | 0.0 |
| BCF318 | 50.0 | 0.0 | 24.9 | 0.0 | 0.0 | 25.1 | 0.0 | 0.0 | 0.0 | 0.0 |
| BCF319 | 50.0 | 0.0 | 0.0 | 0.0 | 25.2 | 0.0 | 24.8 | 0.0 | 0.0 | 0.0 |
| BCF320 | 50.0 | 25.2 | 0.0 | 0.0 | 0.0 | 0.0 | 0.0 | 24.8 | 0.0 | 0.0 |
| BCF321 | 75.4 | 0.0 | 0.0 | 0.0 | 0.0 | 0.0 | 0.0 | 0.0 | 0.0 | 24.6 |
| BCF322 | 50.0 | 0.0 | 0.0 | 0.0 | 0.0 | 20.0 | 30.0 | 0.0 | 0.0 | 0.0 |
| BCF323 | 50.0 | 0.0 | 0.0 | 23.2 | 0.0 | 0.0 | 0.0 | 0.0 | 26.8 | 0.0 |
| BCF324 | 52.0 | 29.0 | 5.0 | 2.4 | 4.2 | 6.4 | 0.4 | 0.0 | 0.3 | 0.3 |
| BCF325 | 50.0 | 0.0 | 0.0 | 0.0 | 0.0 | 0.0 | 0.0 | 50.0 | 0.0 | 0.0 |
| BCF326 | 50.0 | 0.0 | 24.8 | 0.0 | 0.0 | 0.0 | 25.2 | 0.0 | 0.0 | 0.0 |
| BCF327 | 50.0 | 0.0 | 0.0 | 0.0 | 11.5 | 13.7 | 12.8 | 0.0 | 11.9 | 0.0 |
| BCF328 | 77.4 | 0.0 | 0.0 | 0.0 | 0.0 | 22.6 | 0.0 | 0.0 | 0.0 | 0.0 |
| BCF329 | 50.0 | 0.0 | 0.0 | 0.0 | 0.0 | 0.0 | 26.2 | 23.8 | 0.0 | 0.0 |
| BCF330 | 50.0 | 0.0 | 23.5 | 0.0 | 0.0 | 0.0 | 0.0 | 0.0 | 0.0 | 26.5 |
| BCF331 | 50.0 | 0.0 | 0.0 | 0.0 | 25.6 | 0.0 | 0.0 | 24.4 | 0.0 | 0.0 |
| BCF332 | 50.0 | 0.0 | 25.7 | 0.0 | 0.0 | 0.0 | 0.0 | 24.3 | 0.0 | 0.0 |
| BCF333 | 50.0 | 0.0 | 25.7 | 0.0 | 0.0 | 0.0 | 0.0 | 0.0 | 24.3 | 0.0 |
| BCF334 | 50.0 | 0.0 | 0.0 | 24.8 | 0.0 | 25.2 | 0.0 | 0.0 | 0.0 | 0.0 |
| BCF335 | 70.5 | 0.0 | 0.0 | 29.5 | 0.0 | 0.0 | 0.0 | 0.0 | 0.0 | 0.0 |
| BCF336 | 50.0 | 0.0 | 26.2 | 23.8 | 0.0 | 0.0 | 0.0 | 0.0 | 0.0 | 0.0 |
| BCF337 | 50.0 | 0.0 | 0.0 | 0.0 | 0.0 | 25.9 | 0.0 | 24.1 | 0.0 | 0.0 |
| BCF338 | 73.3 | 26.7 | 0.0 | 0.0 | 0.0 | 0.0 | 0.0 | 0.0 | 0.0 | 0.0 |
| BCF339 | 58.4 | 0.0 | 1.7 | 9.2 | 8.8 | 8.6 | 0.0 | 0.0 | 0.0 | 13.3 |

TABLE 8-continued

| Glass Identifier | $B_2O_3$ | $Li_2O$ | $RbO_2$ | $Na_2O$ | SrO | ZnO | $CaF_2$ | NaF | KF | $SnF_2$ |
|---|---|---|---|---|---|---|---|---|---|---|
| BCF340 | 50.0 | 26.4 | 0.0 | 23.6 | 0.0 | 0.0 | 0.0 | 0.0 | 0.0 | 0.0 |
| BCF341 | 50.0 | 0.0 | 0.0 | 0.0 | 0.0 | 0.0 | 25.3 | 0.0 | 0.0 | 24.7 |
| BCF342 | 50.0 | 0.0 | 0.0 | 0.0 | 24.8 | 0.0 | 0.0 | 0.0 | 25.2 | 0.0 |
| BCF343 | 59.5 | 13.4 | 0.0 | 0.0 | 0.0 | 0.0 | 8.7 | 0.0 | 9.2 | 9.2 |
| BCF344 | 50.0 | 0.0 | 0.0 | 0.0 | 0.0 | 25.1 | 0.0 | 0.0 | 0.0 | 24.9 |
| BCF345 | 50.0 | 22.6 | 0.0 | 0.0 | 0.0 | 27.4 | 0.0 | 0.0 | 0.0 | 0.0 |
| BCF346 | 50.0 | 0.0 | 0.0 | 0.0 | 24.9 | 25.1 | 0.0 | 0.0 | 0.0 | 0.0 |
| BCF347 | 50.0 | 0.0 | 0.0 | 25.8 | 24.2 | 0.0 | 0.0 | 0.0 | 0.0 | 0.0 |
| BCF348 | 73.9 | 0.0 | 0.0 | 0.0 | 0.0 | 0.0 | 26.1 | 0.0 | 0.0 | 0.0 |
| BCF349 | 50.0 | 0.0 | 24.9 | 0.0 | 25.1 | 0.0 | 0.0 | 0.0 | 0.0 | 0.0 |
| BCF350 | 50.0 | 0.0 | 0.0 | 27.6 | 0.0 | 0.0 | 22.4 | 0.0 | 0.0 | 0.0 |
| BCF351 | 73.9 | 0.0 | 26.1 | 0.0 | 0.0 | 0.0 | 0.0 | 0.0 | 0.0 | 0.0 |
| BCF352 | 73.5 | 0.0 | 0.0 | 0.0 | 26.5 | 0.0 | 0.0 | 0.0 | 0.0 | 0.0 |
| BCF353 | 50.0 | 11.0 | 0.0 | 13.1 | 0.0 | 11.6 | 10.5 | 3.8 | 0.0 | 0.0 |
| BCF354 | 50.0 | 0.0 | 0.0 | 24.9 | 0.0 | 0.0 | 0.0 | 25.1 | 0.0 | 0.0 |
| BCF357 | 50.0 | 0.0 | 0.0 | 0.0 | 24.9 | 25.1 | 0.0 | 0.0 | 0.0 | 0.0 |
| BCF362 | 73.9 | 0.0 | 26.1 | 0.0 | 0.0 | 0.0 | 0.0 | 0.0 | 0.0 | 0.0 |
| BCF363 | 73.5 | 0.0 | 0.0 | 0.0 | 26.5 | 0.0 | 0.0 | 0.0 | 0.0 | 0.0 |
| BCF364 | 50.0 | 11.0 | 0.0 | 13.1 | 0.0 | 11.6 | 10.5 | 3.8 | 0.0 | 0.0 |

The exemplary glass compositions, and additional compositions, shown in Table 8 were selected based on a design of mixtures (Design Expert 8.0.4, Stat-Ease Inc.) to evaluate the effect of various ranges of components on the glass composition.

The glass compositions were synthesized as described above. Briefly, sufficient amounts of analytical grade reagents (Sigma Aldrich, Canada) needed to form each of the above compositions were weighed. The individual formulations were mixed for 60 mins to ensure homogeneity. Each precursor blend was placed and packed in 50 mL platinum crucibles (Johnson Matthey, Noble Metals, Pennsylvania). The pack crucible was then placed in a furnace (Carbolite, RHF 1600) at room temperature. The furnace was heated (25° C./minute) to an initial dwelling temperature of 600° C. and held for 60 minutes. The temperature was then ramped (20° C./minute) to a final dwelling temperature of 1,100° C. and held for 60 minutes. On removal, each glass melt was quenched between two stainless steel plates.

The following compositions are specific examples of compositions that formed glasses under the above-described quench conditions, such conditions represent one option for standard quench conditions that would be suitable for a production-scale process.

TABLE 9

Examples of compositions that formed glasses under described quench conditions

| Glass Identifier | $B_2O_3$ | $Li_2O$ | $RbO_2$ | $Na_2O$ | SrO | ZnO | $CaF_2$ | NaF | KF | $SnF_2$ |
|---|---|---|---|---|---|---|---|---|---|---|
| BCF301 | 50 | 23.2 | 0 | 0 | 0 | 0 | 26.8 | 0 | 0 | 0 |
| BCF308 | 50 | 0 | 0 | 0 | 0 | 24.3 | 0 | 0 | 25.7 | 0 |
| BCF313 | 50 | 25.4 | 0 | 0 | 0 | 0 | 0 | 0 | 24.6 | 0 |
| BCF315 | 50 | 24.2 | 25.8 | 0 | 0 | 0 | 0 | 0 | 0 | 0 |
| BCF320 | 50 | 0 | 24.9 | 0 | 0 | 25.1 | 0 | 0 | 0 | 0 |
| BCF321 | 50 | 0 | 0 | 0 | 25.2 | 0 | 24.8 | 0 | 0 | 0 |
| BCF322 | 50 | 25.2 | 0 | 0 | 0 | 0 | 0 | 24.8 | 0 | 0 |
| BCF324 | 50 | 0 | 0 | 0 | 0 | 20.0 | 30.0 | 0 | 0 | 0 |
| BCF342 | 50 | 0 | 0 | 0 | 0 | 25.9 | 0 | 24.1 | 0 | 0 |
| BCF357 | 50 | 0 | 0 | 0 | 24.9 | 25.1 | 0 | 0 | 0 | 0 |
| BCF364 | 50 | 11.0 | 0 | 13.1 | 0 | 11.6 | 10.5 | 3.8 | 0 | 0 |

The resulting quenched glasses for the exemplary compositions listed in Table 9 had the following bulk properties:

TABLE 10

Bulk properties for some exemplary glasses

| Glass Identifier | Density (g/cm³) | % Crystallinity | Glass Transition Temp (° C.) | | |
|---|---|---|---|---|---|
| | | | Onset | Inflection | Fictive |
| BCF301 | 2.5879 (±0.03) | 1.20 | 425.8 | 450.7 | 451 |
| BCF308 | 2.7420 (±0.004) | 0.9 | 415.5 | 435.7 | 426 |
| BCF313 | 2.3125 (±0.01) | 1.3 | 379.1 | 392.2 | 387 |
| BCF315 | 2.8084 (±0.07) | 0.7 | 310.3 | 310.6 | 294 |
| BCF320 | 3.1301 (±0.04) | 0.4 | 410.0 | 410.2 | 436 |
| BCF321 | 3.2655 (±0.009) | 0.9 | 512.6 | 526.0 | 521 |
| BCF322 | 2.3414 (±0.008) | 0.5 | 387.2 | 398.2 | 352 |
| BCF324 | 3.1335 (±0.009) | 2.1 | 530.4 | 519.3 | 546 |
| BCF342 | 2.9056 (±0.01) | 1.8 | 462.3 | 474.6 | 482 |
| BCF357 | 3.5263 (±0.004) | 0.5 | 552.2 | 578.2 | 605 |
| BCF364 | 2.6382 (±0.02) | 1 | 391.6 | 401.8 | 402 |

The resulting quenched glasses for the exemplary compositions listed in Table 9 were ground/milled separately within a planetary micro mill (Pulverisette 7, Fritsch, Germany) and sieved with ASTM E-11 compliant sieves (Cole Palmer, U.S.A) to obtain particles of <25 μm.

The particle size distribution for the exemplary glasses listed in Table 9 is shown in Table 11. BCF315, BCF326 degraded in the deionized water too quickly to obtain accurate particle size measurements.

TABLE 11

| Particle size distribution (μm) | | | |
|---|---|---|---|
| Glass Identifier | Dx (10) | Dx (50) | Dx (90) |
| BCF301 | 3.15 | 11.00 | 24.30 |
| BCF308 | 3.07 | 9.71 | 22.10 |
| BCF313 | 4.70 | 11.00 | 21.00 |
| BCF315 | * | * | * |
| BCF320 | 3.11 | 9.23 | 20.60 |
| BCF321 | 2.94 | 9.73 | 20.70 |
| BCF322 | 3.96 | 10.40 | 21.10 |
| BCF324 | 3.63 | 9.39 | 19.80 |
| BCF342 | 3.36 | 10.90 | 24.30 |
| BCF357 | 2.79 | 9.66 | 21.90 |
| BCF364 | 2.9 | 8.73 | 19.8 |

The particles of the exemplary glasses listed in Table 9 were evaluated for mass loss and fluoride release in a buffered saline solution at 1, 4 and 24 hours. Samples were prepared in 15 mL conical test tubes (n=3), which were weighed and recorded. 0.1 grams of each glass powder (<25 microns) were separately weighed out and placed in 10 mL TRIS buffered saline (BioUltra, Sigma Aldrich, Canada) in the weighed 15 mL Falcon tubes. The tubes were sealed with parafilm before being placed in a shaking incubator at 37° C. and agitated at 120 rpm for four separate time points: 5 mins, 30 mins, 1 hr, 3 hrs, 24 hours and 48 hours. After the specified time points elapsed, the tubes were removed from the incubator and the solutions were immediately centrifuged (Eppendorf, Centrifuge 5702) at 3.0 RCF/4.4 RPM for 15 minutes. The supernatant was decanted into fresh 15 mL Falcon tubes. Additionally, samples of the 48-hour incubated powders were re-suspended in 10 mL of fresh TRIS buffered saline by vortex mixing, and allowed to incubate for an additional 8 hours (for a total of 56 hours of incubation). The re-incubated powders were processed in an identical manner as the other samples. The pellets were dried in an oven at 50° C. in their respective Falcon tubes.

The release of fluoride ions was measured using an Accumet AB250 pH/ion selective meter equipped with an Fluoride electrode (Fisher Scientific). To calibrate the probe, 6 standard solutions were prepared using a fluoride analytical standard specifically for ion selective electrodes (NaF, 0.1 F, Sigma Aldrich, Canada). The fluoride concentrations of the standards were synthesized as follows: 1000 ppm, 100 ppm, 10 ppm, 1 ppm, 0.1 ppm and 0.01 respectively, using TRIS buffered saline (BioUltra, Sigma Aldrich, Canada) as the solvent. TISAB concentrate (4.5 mL) was added to each standard before calibration (as per manufacturer's instructions). Once the probe was calibrated, the slope of the standard was checked to ensure it was within range from the instructions of use. TISAB concentrate (1.0 mL) was added to the decanted supernatants and were then measured for its fluoride concentrations using the calibrated probe. The ion concentrations are reported as the average±SD.

The mass losses and ppm values of released fluoride are shown in Table 12. BCF314 degraded completely in the buffered saline solution before the 1 hour time point, and additionally did not include any source of fluoride.

TABLE 12

Mass loss and fluoride release for exemplary glasses at 1, 4 and 24 hours

| | Mass Loss (%) | | | Fluoride Release (ppm) | | |
|---|---|---|---|---|---|---|
| Glass Identifier | 1 | 4 | 24 | 1 | 4 | 24 |
| BCF301 | 45.23 | 36 | 62 | 22 | 26 | 24 |
| BCF308 | 13.74 | 13 | 14 | 50 | 54 | 67 |
| BCF313 | 100% | N/A | N/A | 270 | N/A | N/A |
| BCF315 | N/A | N/A | N/A | N/A | N/A | N/A |
| BCF320 | 56.43 | 63 | 58 | 1 | 1.2 | 1 |
| BCF321 | 38.55 | 59 | 65 | 21 | 21 | 18 |
| BCF322 | 100% | N/A | N/A | 329 | N/A | N/A |
| BCF324 | 7.554 | 20 | 13 | 15 | 11 | 6.7 |
| BCF342 | 12.37 | 8.1 | 18 | 22 | 22 | 29 |
| BCF357 | 14.66 | 13 | 18 | 0 | 0.1 | 0 |
| BCF364 | 13.488 | 21 | 12 | 30 | 32 | 31 |

The compositions listed in Table 8 reflect a design space. The results of the tested compositions provided the following equations, which may allow for the relative comparison of different compositions and/or which may be useful to identify trends associated with different components of the compositions. While experimental and modeling error prevents absolute prediction of glass properties, the equations may be used to guide and refine glass composition design. When used together, these models may help suggest which factors may be traded off in the tailoring of multi-component compositions within the tested composition space. In the following equations, the values for the listed components are in percentages (not fractions or decimals). For example, 50 mol % of $B_2O_3$ would be "50" (and not "0.5").

Glass is generally expected to form under the tested quench conditions if the following formula is less than or equal to 1.60:

$$(2.01*e^y+0.99)/(1+e^y)$$

where $y=-0.086622*[B_2O_3]+0.14169*[Li_2O]-0.565849*[ZnO]+0.192175*[Na_2O]-0.461537*[CaF_2]+0.036636*[KF]+0.00365*[NaF]+0.191201*[SnF_2]+0.192612*[RbO_2]+0.199999*[SrO]+0.01393*[B_2O_3]*[ZnO]+0.012239*[B_2O_3]*[CaF_2]-0.012412*[Li_2O]*[CaF_2]-0.013904*[Li_2O]*[RbO_2]-0.010857*[ZnO]*[CaF_2]-0.013296*[ZnO]*[RbO_2]-0.010699*[ZnO]*[SrO]+0.010128*[CaF_2]*[KF]-0.012103*[CaF_2]*[SrO]$.

The density of a glass may be generally predicted using the following formula: $\rho=0.018783*[B_2O_3]+0.026444*[Li_2O]+0.046191*[ZnO]+0.033814*[Na_2O]+0.039196*[CaF_2]+0.026997*[KF]+0.029458*[NaF]+0.049441*[SnF_2]+0.047057*[RbO_2]+0.054984*[SrO]$. Glass densities from about 1.3 g/cm³ to about 2.2 g/cm³ may particularly useful in non-aqueous oral care formulations. Glycerol and silica, which are the primary liquid and solid components of a non-aqueous toothpaste, have densities of 1.3 and 2.2 g/cm³, respectively.

The glass transition temperature ($T_g$) may be generally predicted using the following formula: $T_g=3.49398*[B_2O_3]+3.66342*[Li_2O]+6.38755*[ZnO]+6.23689*[Na_2O]+6.43079*[CaF_2]+3.31695*[KF]+5.04074*[NaF]+9.88761*[SnF_2]+3.29777*[RbO_2]+10.51264*[SrO]$. It should be understood that phase separated glasses may present multiple glass transitions, the magnitude of which is not necessarily representative of the volume distribution of the phases. While the above equation predicts the onset of a glass transition, the predicted onset may not be the predominant glass transition of the composition if phase separation occurs. Accordingly, a predicted glass transition temperature may be significantly different from the measured predominant glass transition temperature.

The equation related to percent of mass loss after 1 hour under the tested conditions is:

$$(100*e^y)/(1+e^y)$$

where $y=0.088098*[B_2O_3]+0.062481*[Li_2O]-0.262486*[ZnO]+0.055442*[Na_2O]-0.165517*[CaF_2]+0.089171*[KF]+0.075875*[NaF]+0.10439*[SnF_2]+0.109897*[RbO_2]-0.089987*[SrO]$. The above equation is highly predictive for identifying glass compositions which demonstrate complete dissolution within 1 hour under the tested conditions, and may be useful for identifying other glasses which degrade under this time frame. Further, although the equation does not provide accurate mass loss estimates for slower degrading compositions, the equation may be useful to predict the relative changes in degradation which could be expected to occur with changes of the composition. Such relative changes may be used as a guide in glass composition design.

The equation related to release of fluoride (in ppm) after 1 hour under the tested conditions is:

$$(2750*e^y)/(1+e^y)$$

where $y=-0.05785*[B_2O_3]-0.158337*[Li_2O]-0.170872*[ZnO]-0.184773*[Na_2O]+0.05638*[CaF_2]+0.101381*[KF]+0.053886*[NaF]-0.307462*[SnF_2]-0.183034*[RbO_2]-0.184126*[SrO]$. Although the above equation does not provide an accurate estimate of the amount of fluoride released for all glass compositions, the model may still be useful to predict the relative changes in fluoride release which could be expected to occur with changes of the composition.

PBF1 was synthesized by: weighing 11.60 g of $B_2O_3$, 5.30 g of $Na_2CO_3$, 2.69 g of MgO, 3.33 g of $CaCO_3$, and 0.7 g of $CaF_2$ (Sigma Aldrich, Canada). The starting materials were mixed for 60 mins to ensure homogeneity. The blend was placed and packed in 50 mL platinum crucibles (Johnson Matthey, Noble Metals, Pennsylvania). The pack crucible was then placed in a furnace (Carbolite, RHF 1600) at room temperature. The furnace was heated (25° C./minute) to an initial dwelling temperature of 600° C. and held for 60 minutes. The temperature was then ramped (20° C./minute) to a final dwelling temperature of 1,200° C. and held for 60 minutes. On removal, the glass melt was quenched between two stainless steel plates. The resulting quenched glasses were ground/milled separately within a planetary micro mill (Pulverisette 7, Fritsch, Germany) and sieved with ASTM E-11 compliant sieves (Cole Palmer, U.S.A) to obtain particles of <25 μm.

Comparative glass compositions (referred to as Comparative Examples (CE) 1 and 2) were synthesized similarly, using: 5.80 g $B_2O_3$, 23.66 g $P_2O_5$, 5.30 g $Na_2CO_3$, 1.34 g MgO, 6.67 g $CaCO_3$, and 0.70 g $CaF_2$ to result in: CE1 with about 25 mol % $B_2O_3$, about 25 mol % $P_2O_5$, about 15 mol % $Na_2O$, about 10 mol % MgO, about 20 mol % CaO, and about 5 mol % $CaF_2$; and 5.80 g $B_2O_3$, 23.66 g $P_2O_5$, 7.07 $Na_2CO_3$, 1.34 g MgO, 5.00 g $CaCO_3$, and 0.70 g $CaF_2$ to result in CE2 with about 25 mol % $B_2O_3$, about 25 mol % $P_2O_5$, about 20 mol % $Na_2O$, about 10 mol % MgO, about 15 mol % CaO, and about 5 mol % $CaF_2$.

The density of the glass powders were measured using an AccuPyc 1340 helium pycnometer (Micromeritics, USA) equipped with a 1 cm³ insert. Prior to use, a standard with a volume of 0.718512 cm³ was used to calibrate the pycnometer. For glass analysis, the insert was packed with about 0.5 to 0.7 grams of glass powder. Three samples of each of the glasses were run and each measurement is the mean of 10 readings.

The density of PBF1 was measured as 2.5951±0.0072 g/cm³. The density of CE1 was measured as 2.7079±0.0021 g/cm³. The density of CE2 was measured as 2.6749±0.0013 g/cm³.

The release of fluoride and the loss of mass was measured for PBF1, CE1 and CE2. Samples were prepared in 15 mL conical test tubes (n=3), which were weighed and recorded. 0.1 grams of each glass powder (<25 microns) were separately weighed out and placed in 10 mL TRIS buffered saline (BioUltra, Sigma Aldrich, Canada) in the weighed 15 mL Falcon tubes. The tubes were sealed with parafilm before being placed in a shaking incubator at 37° C. and agitated at 120 rpm for four separate time points: 5 mins, 30 mins, 1 hr, 3 hrs, 24 hours and 48 hours. After the specified time points elapsed, the tubes were removed from the incubator and the solutions were immediately centrifuged (Eppendorf, Centrifuge 5702) at 3.0 RCF/4.4 RPM for 15 minutes. The supernatant was decanted into fresh 15 mL Falcon tubes. Additionally, samples of the 48-hour incubated powders were re-suspended in 10 mL of fresh TRIS buffered saline by vortex mixing, and allowed to incubate for an additional 8 hours (for a total of 56 hours of incubation). The re-incubated powders were processed in an identical manner as the other samples. The pellets were dried in an oven at 50° C. in their respective Falcon tubes.

The release of fluoride ions was measured using an Accumet AB250 pH/ion selective meter equipped with an Fluoride electrode (Fisher Scientific). To calibrate the probe, 6 standard solutions were prepared using a fluoride analytical standard specifically for ion selective electrodes (NaF, 0.1 F, Sigma Aldrich, Canada). The sodium fluoride concentrations of the standards were synthesized as follows: 1000 ppm, 100 ppm, 10 ppm, 1 ppm, 0.01 ppm and 0.001 respectively, using TRIS buffered saline (BioUltra, Sigma Aldrich, Canada) as the solvent. TISAB concentrate (4.5 mL) was added to each standard before calibration (as per manufacturer's instructions). Once the probe was calibrated, the slope of the standard was checked to ensure it was within range from the instructions of use. TISAB concentrate (1.0 mL) was added to the decanted supernatants and were then measured for its fluoride concentrations using the calibrated probe. The ion concentrations are reported as the average±SD.

The amount of fluoride ion released by PBF1 was measured as: 89±2 ppm at 5 mins; 94±3 ppm at 30 mins; 105±5 ppm at 1 hour; and 94±7 ppm at 3 hours. There was no measurable fluoride ion released by CE1 or CE2.

The loss of mass was calculated by comparing the mass of the dried samples after their exposure to the TRIS buffered saline to the initial mass of the samples. The mass loss for PBF1 was: 42.0±2.1% after 5 minutes; 47.3±2.7% after 30 minutes; 51.5±4.3% after 1 hour; 41.7±5.7% after 3 hours; 70.1±6.8% after 24 hours; and 100% after 48 hours.

The particle size of seven different samples of PBF1 was measured using a Malvern Mastersizer 3000 model laser diffraction particle size analyzer. Glass particles were separately suspended in distilled water to obtain an obscuration value between 2-5%. Prior to analysis, the glass powder was stored in a vacuum desiccator and was removed for analysis for 3×5 runs lasting approximately 20 secs/run. Suspensions were measured using both a blue (λ=470 nm) and red (λ=632.8 nm) laser (n=5).

TABLE 13

Particle size distribution for PBF1

|  | Dx10 (μm) | Dx50 (μm) | Dx90 (μm) |
|---|---|---|---|
| PBF1.1 | 3.18 | 11.9 | 26.9 |
| PBF1.2 | 3.44 | 10.5 | 22.2 |
| PBF1.3 | 3.26 | 9.99 | 22.1 |
| PBF1.4 | N/A | N/A | N/A |
| PBF1.5 | 3.35 | 12.3 | 27.4 |
| PBF1.6 | 3.44 | 10.3 | 22.3 |
| PBF1.7 | 4.84 | 13.2 | 27.1 |

Apatite formation in simulated body fluid was confirmed for PBF1, but was not evident with CE1 or CE2. Simulated Body Fluid was synthesized as per the methods and instructions published by Kokubo and Takadama (Kokubo, T. and Takadama, H. Biomaterials (2006) 27:15, pp 2907-2915).

1 L batches of SBF were prepared in 1000 mL Nalgene bottle (FEP bottle). The prepared SBF was stored at room temperature for 24 hrs immediately after synthesis to ensure stability before experimental use. The SBF was preserved in a Nalgene bottle with the lid on tightly and kept at 6° C. if not needed immediately (for up to 30 days for experimental use).

As per the TCO4 method (published in Magon, A. L. B., Kim, T. B., Valliant, E. M. et al. *J Mater Sci: Mater Med* (2015) 26:115) 0.75 g of glass powder of each glass composition (n=3) was immersed in 50 mL of SBF, as synthesized per above, in polyethylene containers. Containers were then placed in an incubating orbital shaker at 37° C. and agitated at 120 rpm for 3 time points: 30 mins, 3 hrs and 12 hrs. After the time points elapsed, each specimen was vacuum filtered with Whatman 42 or 5 grade filter paper (particle retention of 2.5 μm) to collect the solid material from the solution. The solids were immediately washed with distilled water and acetone to stop any further reaction.

Figure 11:
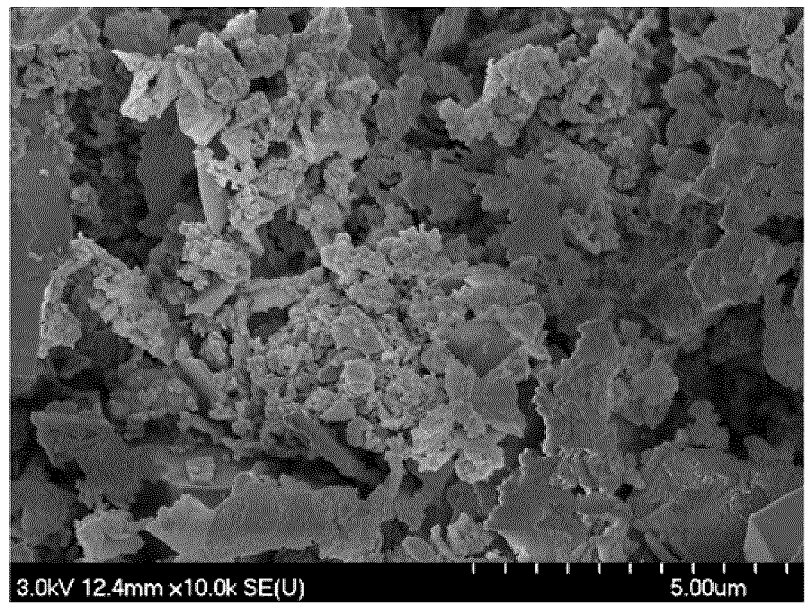
FIG. 11 is an image from a scanning electron microscope of an exemplary glass composition according to the present disclosure after 30 minutes in simulated body fluid (SBF) at 37° C.
Figure 12:
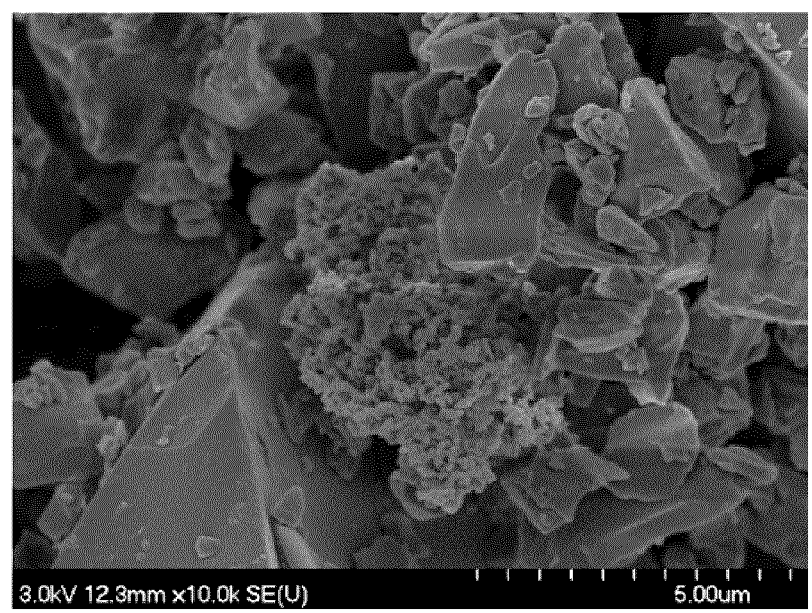
FIG. 12 is an image from a scanning electron microscope of an exemplary glass composition according to the present disclosure after 3 hours in simulated body fluid (SBF) at 37° C.
Figure 13:
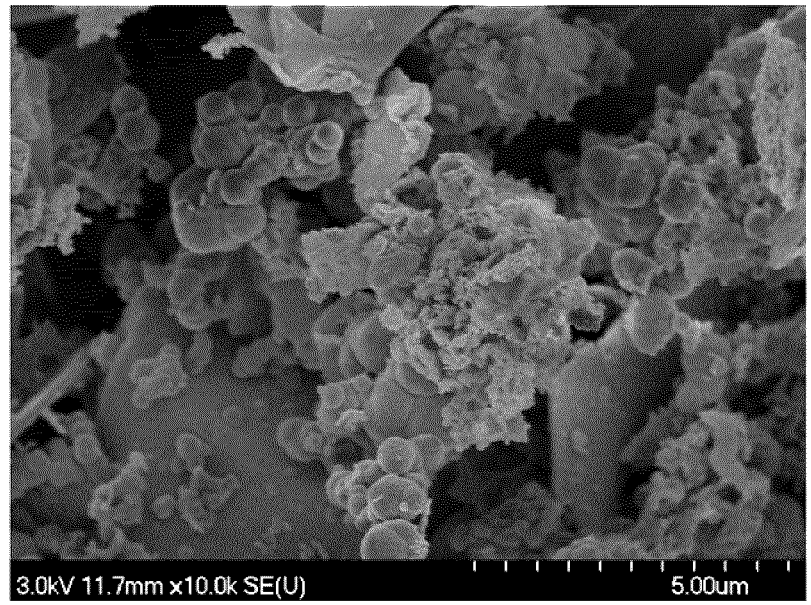
FIG. 13 is an image from a scanning electron microscope of an exemplary glass composition according to the present disclosure after 12 hours in simulated body fluid (SBF) at 37° C.
Figure 14:
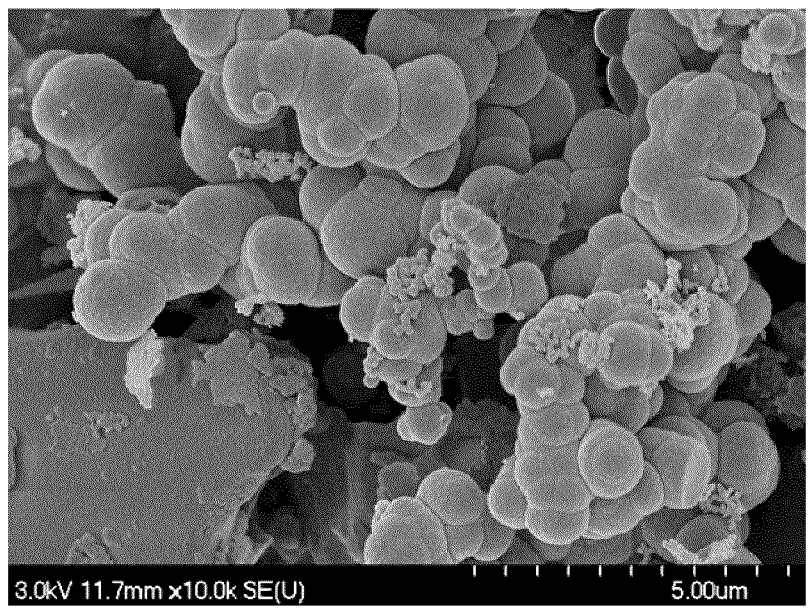
FIG. 14 is another photograph from a scanning electron microscope of an exemplary glass composition according to the present disclosure after 12 hours in simulated body fluid (SBF) at 37° C.

The filtered specimens were dried in a vacuum desiccator for further analysis. Imaging of each specimen was performed using a Hitachi S-4700 FEG (Hitachi, Chula Vista, Ca) scanning electron microscope operating at 3 KV and 15 mA under magnification of 1000× and 10000×. Samples were mounted on stubs using double sided carbon tape and sputter coated with gold-palladium for 70 s (Leica EM ACE200, Wetzlar, Germany). The scanning electron microscope images of PBF1 at 30 minutes, 3 hours and 12 hours are shown in FIGS. 11 to 14.

PBF1 was also assessed for dentin tubule occlusion by developing an application protocol and statistical analysis of SEM images graded by two assessors according to a categorical occlusion scale. Sections of human dentin (about 1 to 1.5 mm thick) were prepared from the crowns of caries-free, unrestored molars, perpendicular to the long axis of the roots, using a diamond disc saw. Each section was etched for 2 minutes with 10% citric acid, followed by water rinsing for 60 seconds, sonication for 2 minutes and a further water rinse for 60 seconds. Each section was placed into a 25 mm diameter mould and covered with 3 mm-deep acrylic resin. Once the resin hardened, the dentin face was polished sequentially with 800, and 2500-grit paper to a mirror finish. Following a deionised water rinse, the surface was etched, sonicated and rinsed once more. Sample integrity, tubule density and patency were once again checked under a light microscope, and then with SEM.

A single dentin sample was assigned to each treatment group. The dentin sample was treated with (i) an unformulated mixture of exemplary glass particles, (ii) a test toothpaste that included a mixture of exemplary glass particles, or (iii) a control toothpaste without any additional glass particles. The unformulated mixture was applied using a non-powder nitrile gloved finger for 10 seconds. The test and control toothpastes were applied to the sample with an electric toothbrush for 10 second. The toothpaste was left for 30 seconds before being rinsed until all visible paste was removed. This was repeated for a total of 4 applications of the toothpaste.

Dentin samples were dried in an oven for 1 hour at 37° C., sputter coated with gold, and visualized using a Phenom ProX Scanning Electron Microscope. Five images at ×3000 magnification were taken of different portions of each sample, in which the tubules were perpendicular to the surface. Each ×3000 micrograph was examined by two single-blinded assessors for the extend of dentin tubule occlusion based on a five-point categorical scale. The grading classification was defined as:
1. Occluded (100% occlusion)
2. Mostly occluded (75% occlusion)
3. Equal (50% occlusion)
4. Mostly unoccluded (25% occlusion)
5. Unoccluded (0% occlusion)

Mean scores for each image were derived from the scores of the two assessors. Standard deviations were calculated, though no formal statistical comparisons were made due to the fact that only one dentin sample was used per treatment group.

Seven different treatment groups were tested, as outlined in Table 14.

TABLE 14

Treatment groups for test of dentin tubule occlusion

| Treatment Group | Test Article | Materials |
|---|---|---|
| 1 | No treatment of dentin sample | N/A |
| 2 | Test Article #1 | 0.1 g PBF1 |
| 3 | Test Article #2 | 0.0125 g PBF1 + 0.25 g Sensodyne ™ Complete Protection (5% w/w) |
| 4 | Test Article #3 | 0.0375 g PBF1 + 0.25 g Sensodyne ™ Complete Protection (15% w/w) |
| 5 | Control Article #1 | 0.25 g Sensodyne ™ Complete Protection |
| 6 | Control Article #2 | 0.25 g Colgate ™ Pro-Relief |
| 7 | Control Article #3 | 0.25 g Sensodyne ™ Repair & Protect |

As discussed above, each sample treatment group was tested on a dentin sample and five SEM micrographs of each sample were taken at ×3000. Each micrograph was categorically assessed by two assessors. The average score for each micrograph, and the five micrographs per sample, were combined to obtain a group mean score and standard deviation (see Table 15).

TABLE 15

Mean occlusion score for different treatment groups

| Treatment Group | Group Mean (±SD) |
|---|---|
| 1 | 4.90 (±0.22) |
| 2 | 1.50 (±0.0) |
| 3 | 2.90 (±1.02) |
| 4 | 2.40 (±0.42) |
| 5 | 3.60 (±0.22) |

TABLE 15-continued

Mean occlusion score for different treatment groups

| Treatment Group | Group Mean (±SD) |
|---|---|
| 6 | 3.60 (±0.22) |
| 7 | 3.20 (±0.45) |

The mean baseline score of 4.90 for treatment group 1 illustrates that virtually all dentin tubules were un-occluded. The mean score of 1.50 for the unformulated PBF1 rubbed directly into the dentin sample illustrates a nearly complete tubule blockage. The treatment groups 5, 6 and 7 (control groups lacking PBF1 or any other glass composition according to the present disclosure) had mean occlusion scores from 3.2 to 3.6. The treatment groups 3 and 4 (commercial toothpaste formulated with 5% or 15% PBF1 w/w) had lower mean occlusion scores, indicating a greater degree of tubule occlusion. The degree of occlusion for the commercially available toothpaste Sensodyne™ Complete Protection increased from about 30% occlusion (score 3.6) to about 50% occlusion (score 2.5) when 15% w/w/of PBF1 was added.

PBF1 was further assessed for dentin tubule occlusion using a 5% w/w PBF1 sodium lauryl sulfate (SLS) paste. In this assessment, the PBF1-toothpaste and control toothpaste were applied to three different dentin samples for each treatment group. The samples were each brushed once for two minutes with the treatment toothpaste. Specifically, each dentin sample was brushed with 0.25 g of a treatment toothpaste for 120 seconds and subsequently rinsed with DI water for 30 seconds. The 5% PBF1-SLS paste resulted in a mean occlusion score of 2.7±0.84. The SLS paste without the PBF1 resulted in a mean occlusion score of 3.80±1.03. A control test using Sensodyne™ Repair & Protect resulted in a mean occlusion score of 3.90±0.66.

PBF1-Na was prepared following the protocols discussed above. Briefly, the glass was synthesized by: weighing 11.05 g of $B_2O_3$, 3.36 g of $Na_2CO_3$, 2.56 g of MgO, 4.77 g of $CaCO_3$, and 1.33 g of NaF (Sigma Aldrich, Canada). The starting materials were mixed for 60 mins to ensure homogeneity. The blend was placed and packed in 50 mL platinum crucibles (Johnson Matthey, Noble Metals, Pennsylvania). The pack crucible was then placed in a furnace (Carbolite, RHF 1400) at room temperature. The furnace was heated (25° C./minute) to an initial dwelling temperature of 600° C. and held for 60 minutes. The temperature was then ramped (20° C./minute) to a final dwelling temperature of 1,200° C. and held for 60 minutes. On removal, the glass melt was quenched between two stainless steel plates. The resulting quenched glasses were ground/milled separately within a planetary micro mill (Pulverisette 6, Fritsch, Germany) and sieved with ASTM E-11 compliant sieves (Cole Palmer, U.S.A) to obtain particles of <25 µm.

The particle size of ten different samples of PBF1-Na was measured as discussed above.

TABLE 16

Particle size distribution for PBF1-Na

| | Dx10 (µm) | Dx50 (µm) | Dx90 (µm) |
|---|---|---|---|
| PBF1-Na.1 | 4.7 | 14.9 | 35.2 |
| PBF1-Na.2 | 4.6 | 14.4 | 31.2 |
| PBF1-Na.3 | 4.2 | 13.3 | 29.9 |

TABLE 16-continued

Particle size distribution for PBF1-Na

| | Dx10 (µm) | Dx50 (µm) | Dx90 (µm) |
|---|---|---|---|
| PBF1-Na.4 | 4.5 | 14.1 | 30.7 |
| PBF1-Na.5 | 4.3 | 12.0 | 26.7 |
| PBF1-Na.6 | 4.4 | 13.9 | 30.5 |
| PBF1-Na.7 | 4.1 | 12.1 | 26.2 |
| PBF1-Na.8 | 4.3 | 12.2 | 25.5 |
| PBF1-Na.9 | 4.0 | 11.8 | 25.7 |
| PBF1-Na.10 | 4.2 | 13.3 | 29.7 |
| Average | 4.3 | 13.2 | 29.1 |

The density, % crystallinity, and glass transition temperatures for the ten different samples were also measured as discussed above.

TABLE 17

Bulk properties for PBF1-Na

| Glass Identifier | Density (g/cm³) | % Crystallinity | Glass Transition Temp (° C.) Onset | Inflection | Fictive |
|---|---|---|---|---|---|
| PBF1-Na.1 | 2.543 (±0.004) | 1.5 | 494.2 | 508.3 | 518.3 |
| PBF1-Na.2 | 2.537 (±0.004) | 1.8 | 492.6 | 506.1 | 519.6 |
| PBF1-Na.3 | 2.546 (±0.003) | 1.8 | 493.7 | 506.6 | 520.6 |
| PBF1-Na.4 | 2.544 (±0.003) | 1.9 | 493.3 | 506.7 | 519.9 |
| PBF1-Na.5 | 2.548 (±0.004) | 1.8 | 492.5 | 505.6 | 520.0 |
| PBF1-Na.6 | 2.544 (±0.004) | 1.8 | 493.0 | 507.0 | 519.3 |
| PBF1-Na.7 | 2.549 (±0.005) | 1.6 | 491.6 | 504.5 | 517.1 |
| PBF1-Na.8 | 2.546 (±0.004) | 1.8 | 491.3 | 506.6 | 520.4 |
| PBF1-Na.9 | 2.545 (±0.004) | 2.0 | 494.1 | 505.3 | 520.4 |
| PBF1-Na.10 | 2.541 (±0.004) | 1.9 | 491.7 | 506.3 | 517.7 |
| Average | 2.544 (±0.005) | 1.8 | 492.8 | 506.3 | 519.3 |

The mass loss and fluoride release after 24 hours for the ten different D 39T samples were also measured as discussed above.

TABLE 18

Mass loss and fluoride release after 24 hours for PBF1-Na

| Glass Identifier | Mass Loss (%) | Fluoride Release (ppm) |
|---|---|---|
| PBF1-Na.1 | 70.3 | 92.0 |
| PBF1-Na.2 | 71.7 | 91.2 |
| PBF1-Na.3 | 71.7 | 88.9 |
| PBF1-Na.4 | 73.3 | 88.4 |
| PBF1-Na.5 | 73.0 | 87.5 |
| PBF1-Na.6 | 73.3 | 95.0 |
| PBF1-Na.7 | 72.0 | 98.8 |
| PBF1-Na.8 | 72.0 | 93.9 |
| PBF1-Na.9 | 72.7 | 94.2 |
| PBF1-Na.10 | 73.3 | 97.6 |
| Average | 72.3 | 92.8 |

In the preceding description, for purposes of explanation, numerous details are set forth in order to provide a thorough understanding of the examples. However, it will be apparent to one skilled in the art that these specific details are not required. Accordingly, what has been described is merely illustrative of the application of the described examples and numerous modifications and variations are possible in light of the above teachings.

Since the above description provides examples, it will be appreciated that modifications and variations can be effected to the particular examples by those of skill in the art. Accordingly, the scope of the claims should not be limited by the particular examples set forth herein, but should be construed in a manner consistent with the specification as a whole.

What is claimed is:

1. A dentin-desensitizing composition comprising:
   (i) glass particles that are from about 1 to about 50 um in size; and
   (ii) a water-free, orally-compatible carrier;
   wherein:
   the glass particles lose at least 5 mass % within 24 hours when exposed to a buffered saline solution;
   the composition of the glass particles consists of:
   about 50 mol % $B_2O_3$,
   about 15 mol % $Na_2O$,
   about 20 mol % MgO,
   about 10 mol % CaO, and
   about 5 mol % NaF, KF, $CaF_2$, $SnF_2$, or any combination thereof.

2. The dentin-desensitizing composition according to claim 1, wherein the composition is a mouthwash, a toothpaste, a dental gel, a prophylaxis paste, a tooth varnish, or a bonding agent.

3. The dentin-desensitizing composition according to claim 1, wherein the orally-compatible carrier is an orally-compatible viscous carrier that has a viscosity from about 100 cP at 30° C. to about 150,000 cp at 30° C.

4. A method of at least temporarily reducing, in an individual, pain associated with sensitive teeth, the method comprising applying the toothpaste, prophylaxis paste, or tooth varnish according to claim 2 to dentin in the individual.

5. The dentin-desensitizing composition according to claim 1, wherein the fluoride is provided as about 5 mol % of $CaF_2$.

6. The dentin-desensitizing composition according to claim 1, wherein at least 75%, at least 85%, or at least 95% of the particles are smaller than 50 μm in size, and/or wherein at least 5% of the particles are smaller than 7 μm in size.

7. The dentin-desensitizing composition according to claim 1, wherein:
   a) at least 5% of the glass particles are smaller than 35 μm in size,
      at least 5% of the particles are smaller than 15 μm in size, and
      at least 5% of the particles are smaller than 7 μm in size; or
   b) at least 5% of the glass particles are from about 15 μm to about 35 μm in size,
      at least 5% of the particles are from about 6 μm to about 15 μm in size, and
      at least 5% of the particles are from about 3 μm to about 7 μm in size.

8. The dentin-desensitizing composition according to claim 1, wherein:
   about 10% of the glass particles are smaller than 5 μm in size,
   about 50% of the glass particles are smaller than 15 μm in size, and
   about 90% of the glass particles are smaller than 30 μm in size.

* * * * *